US006228641B1

(12) United States Patent
Jallal et al.

(10) Patent No.: US 6,228,641 B1
(45) Date of Patent: May 8, 2001

(54) DIAGNOSIS AND TREATMENT OF PTP04 RELATED DISORDERS

(75) Inventors: Bahija Jallal, Menlo Park; Gregory D. Plowman, San Carlos, both of CA (US)

(73) Assignee: Sugen, Inc., Redwood City, CA (US)

( * ) Notice: Subject to any disclaimer, the term of this patent is extended or adjusted under 35 U.S.C. 154(b) by 0 days.

(21) Appl. No.: 09/081,345

(22) Filed: May 19, 1998

Related U.S. Application Data

(60) Provisional application No. 60/047,222, filed on May 20, 1997.

(51) Int. Cl.$^7$ .............................. C12N 5/10; C07H 21/04; C07H 21/02
(52) U.S. Cl. ................ 435/325; 536/23.5; 536/23.4; 536/24.1; 435/69.1; 435/70.1; 435/320.1
(58) Field of Search ................................ 536/23.5, 23.4, 536/23.2, 24.1, 24.3, 24.31; 435/69.1, 70.1, 70.3, 71.1, 320.1, 325

(56) References Cited

U.S. PATENT DOCUMENTS

| | | |
|---|---|---|
| 4,343,940 | 8/1982 | Kreighbaum et al. . |
| 4,376,110 | 3/1983 | David et al. . |
| 4,447,608 | 5/1984 | Jones et al. . |
| 4,757,072 | 7/1988 | Kabbe et al. . |
| 4,945,050 | 7/1990 | Sanford et al. . |
| 5,168,050 | * 12/1992 | Hammonds, Jr. et al. . |
| 5,217,999 | 6/1993 | Levitzki et al. . |
| 5,283,173 | 2/1994 | Fields et al. . |
| 5,302,606 | 4/1994 | Spada et al. . |
| 5,316,553 | 5/1994 | Kaul et al. . |
| 5,330,992 | 7/1994 | Eissenstat et al. . |
| 5,602,171 | 2/1997 | Tang et al. . |

FOREIGN PATENT DOCUMENTS

| | | |
|---|---|---|
| 0 520 722 A1 | 12/1992 | (EP) . |
| 0 562 734 A1 | 9/1993 | (EP) . |
| 0 566 226 A1 | 10/1993 | (EP) . |
| 91/15495 | 10/1991 | (WO) . |
| 92/20642 | 11/1992 | (WO) . |
| 92/21660 | 12/1992 | (WO) . |
| 93/09236 | 5/1993 | (WO) . |
| 94/03427 | 2/1994 | (WO) . |
| 94/14808 | 7/1994 | (WO) . |
| 94/23039 | 10/1994 | (WO) . |
| 96/22976 | 8/1996 | (WO) . |

OTHER PUBLICATIONS

Matthews, R.J. et al., Characterization of hematopoietic intracellular protein tyrosine phosphatases: description of a phosphatase containing an SH2 domain and another enriched in proline–, glutamic acid–, serine–, and threonine–rich sequences. Molecula, May 1992.*
Accession No. P29352 of SWISS–PROT35 database, Feb. 1996.*
Accession No. M90388 of GENBANK111 database, May 1992.*

Abe et al., "Molecular Characterization of a Novel Metabotropic Glutamate Receptor mGluR5 Coupled to Inositol Pohosphate/$Ca^{2+Signal}$," *J. Biol. Chem.* 267(19):13361–13368 (1992).
Allen et al., "Modulation of CD4 by suramin," *Clin. Exp. Immunol.* 91:141–146 (1991).
Altschul et al., "Basic Local Alignment Search Tool," *J. Mol. Biol.* 215:403–410 (1990).
Anafi et al., "Tyrphostin–Induced Inhibition of p210$^{bcr-abl}$ Tyrosine Kinase Activity Induces K562 to Differentiate," *Blood* 82:3524–3529 (1993).
Ausubel et al., Index to *Current Protocols in Molecular Biology* (1989).
Baker et al., "Induction of acetylcholine receptor clustering by native polystyrene beads," *Journal of Cell Science* 102:543–555 (1992).
Barker et al., "In vitro activity of non–glutamate containing quinazoline–based thymidylate synthase inhibitors," *Proceedings of the American Association for Cancer Research* 32:327 at abstract No. 1939 (1991).
Benoist and Chambon, "In vivo sequence requirements of the SV40 early promoter region," *Nature* 290:304–310 (1981).
Bertino, "Toward Improved Selectivity in Cancer Chemotherapy: The Richard and Hinda Rosenthal Foundation Award Lecture," *Cancer Research* 39:293–304 (1979).
Bilder et al., "Tyrphostins inhibit PDGF–induced DNA synthesis and associated early events in smooth muscle cells," *Am. J. Physiol.* 260(Cell Physiol.29):C721–C730 (1991).
Bollon et al., "DNA Transformation Efficiency of Various Bacterial and Yeast Host–Vector Systems," *J. Clin. Hematol. Oncoll.* 10:39–48 (1980).
Botstein et al., "Making Mutations In Vitro and Putting Them Back Into Yeast," *Miami Wntr. Symp.* 19:265–274 (1982).
Brinster et al., "Factors Affecting the Efficiency of Introducing Foreign DNA into Mice by Microinjecting Eggs," *Proc. Natl. Acad. Sci. USA* 82:4438–4442 (1985).
Broach, "The Yeast Plasmid 2$\mu$ Circle," *Cell* 28:203–204 (1982).

(List continued on next page.)

*Primary Examiner*—Anthony C. Caputa
*Assistant Examiner*—Anne L. Holleran
(74) *Attorney, Agent, or Firm*—Foley & Lardner

(57) ABSTRACT

The present invention relates to PTP04 polypetides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for PTP04 related diseases or conditions characterized by an abnormal interaction beteeen a PTP04 polypeptide and a PTP04 binding partner.

15 Claims, 3 Drawing Sheets

OTHER PUBLICATIONS

Brunton et al., "Anti–tumour activity of novel tryphostins in breast cancer cells," *Proceedings of the American Association for Cancer Research* 33:558 at abstract No. 3335 (1992).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bullock et al., *Techniques in Immunocytochemistry*, Academic Press, Orlando, FL vol. 1 (1982), vol. 2 (1983), vol. 3 (1985) Indexes Only.

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase p56$^{lck\ 1}$," *Journal of Medicinal Chemistry* 36(4):425–432 (1993).

Campbell, *Monoclonal Antibody Technology: Laboratory Tchniques in Biochemistry and Molecular Biology*, Elsevier Science Publishers, Amsterdam, The Netherlands, (1984) Index Only.

Capecchi MR, "High Efficiency by Direct Microinjection of DNA into Cultured Mammalian Cells," *Cell* 22:479–88 (1980).

Capecchi, "Altering the Genome by Homologous Recombination," *Science* 244:1288–1292 (1989).

Cenatiempo, "Prokaryotic Gene Expression In Vitro: Transcription—Translation Coupled Systems," *Biochimie* 68:505–516 (1986).

Chard, "An Introduction to Radioimmunoassay and Related Techniques," Elsevier Science Publishers, Amsterdam, The Netherlands (1987) Index Only.

Chater et al., In: *Sixth International Symposium on Actinomycetales Biology*, Akademiai Kaido, Budapest, Hungary pp. 45–54, 1985.

Chen and Okayama, "High–Efficiency Transformation of Mammalian Cells by Plasmid DNA," *Molecular and Cellular Biology* 7(8):2745–2752 (1987).

Chu G., et al., "Electroporation for the Efficient Transfection of Mammalian Cells with DNA," *Nucleic Acids Res.*, 15:1311–26 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular –Type Platelet–Derived Growth Factor Receptor Tyrosine Kinase, "*J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Engvall et al., "Enzyme–Linked Immunosorbent Assay, Elisa," *J. Immunol.*, 109:129 (1972).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Fingl and Woodbury, "Chapter 1—General Principles," in *The Pharmacological Basis of Therapeutics* 5th edition, Goodman and Gilman editors, MacMillan Publishing Co., Inc., New York , pp. 1–46 (1975).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a –Substituted Benzylidenemalononitrile 5–S–Aryltryphostins," *J. Med. Chem.* 36:3556–3564 (1993).

Gilman et al., "Isolation of Sigma–28–Specific Promoters from Bacillus Subtilis DNA," *Gene* 32:11–20 (1984).

Glick, "Factors Affecting the Expression of Foreign Proteins in *Escherichia coli,*" *J. Ind. Microbiot.* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18:415–441 (1984).

Hamer et al., "Regulation In Vivo of a Cloned Mammalian Gene: Cadmium Induces the Transcription of a Mouse Metallothionein Gene in SV40 Vectors," *J. Mol. Appl. Gen.* 1:273–288 (1982).

Hanks and Hunter, "The Eukaryotic Protein Kinase Superfamily: Kinase (Catalytic) Domain Structure and Classification," *FASEB J* 9:576–595 (1995).

Haslam et al., "Pleckstrin Domain Homology," *Nature* 363:309 (1993).

Houdebine and Chourrout, "Transgenesis in Fish," *Experientia* 47:891–897 (1991).

Hurby et al., in *Synthetic Peptides: A User's Guide*, edited by Grant, Washington University School of Medicine, W.H. Freeman and Company, New York, pp. 289–307 (1992).

Innis et al., *PCR Protocols: A Guide to Methods and Applications*, edited by Michael A. Innis et al., Academic Press, San Diego (1990) (Table of Contents Only).

Jackman, "ICI D1694, a Quinazoline Antifolate Thymidylate Synthase Inhibitor That Is a Potent Inhibitor of L1210 Tumor Cell Growth in Vitro and In Vivo: A New Agent for Clinical Study," *Cancer Research* 51:5579–5586 (1991).

Jakoby et al., *Meth. Enzym.* vol. LVIII, pp. 574–584, 1979.

Jasny, "Insect Viruses Invade Biotechnology," *Science* 238:1653 (1987).

John et al., "Plasmids as Epidemiologic Markers in Nosocomial Gram–Negative Bacilli: Experience at a University and Review of the Literature," *Rev. Infect. Dis.* 8:693–704 (1986).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–8 (1989).

Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).

Kendall et al., "Plasmid Transfer in Streptomyces Lividans: Identification of a kil–kor System Associated with the Transfer Region of pIJ101," *J. Bacteriol.* 169:4177–4183 (1987).

King et al., "Site–specific dephosphorylation and deactivation of the human insulin receptor tyrosine kinase by particulate and soluble phosphotyrosyl protein phosphatases," *Biochem. J.* 275:413–418 (1991).

Köhler (Kohler) and Milstein, "Continuous cultures of fused cells secreting antibody of predefined specificity," *Nature* 256:495–497 (1975).

Krueger et al., *Proc. Natl. Acad. Sci. USA* 89:7417–7421 (1992).

Kuo et al., "Effects of signalling transduction modulators on the transformed phenotypes in v–H–ras–transformed NIH 3T3 cells," *Cancer Letters* 74:197–202 (1993).

Lee and Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tyrphostins: tyrosine kinase blockers as novel antiproliferative agents and dissectors of signal transduction," *FASEB J.* 6:3275–3282 (1992).

Ley and Seng, "Synthesis Using Benzofuroxan," *Synthesis* 1975:415–422 (1975) Abstract Only.

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

Maguire et al., "A new series of PDGF Receptor Tyrosine Kinase Inhibitors: 3–Substituted Quinoline Derivatives," *J. Med. Chem.* 37:2129–2137 (1994).

Maniatis, In: *Cell Biology: A Comprehensive Treatise*, vol. 3 Gene Sequences Expression, Academic Press, NY, pp. 563–608 (1980).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

Mayer and Baltimore, "Signalling Through SH2 and SH3 Domains," *Trends Cell. Biol.* 3:8 (1993).

Mayer et al., "A novel viral oncogene with structural similarity to phospholipase C," *Nature* 332:272–275 (1988).

McKnight, "Functional Relationships between Transcriptional Control Signals of the Thymidine Kinase Gene of Herpes Simplex Virus," *Cell* 31:355–365 (1982).

Miller et al., In: *Genetic Engineering* (1986) Setlow, J. K., et al., eds., Plenum, vol. 8, pp. 277–297.

Miller, "Human gene therapy comes of age," *Nature* 357:455–460 (1992).

Miller, A.D. & Rosman, G.J., "Improved Retorviral Vectors for Gene Transfer and Expression," *Biotechniques* 7:980–988 (1989).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mulligan, "The Basic Science of Gene Therapy," *Science* 260:926–932 (1993).

Nelson, "Detection of Acridinium Esters by Chemiluminescence," *Nonisotopic DNA Probe Techniques*, ed. Larry J. Kricka, (San Diego: Academic Press, Inc.) pp. 275–310 (1992).

Okayama, "A cDNA Cloning Vector That Permits Expression of cDNA Inserts in Mammalian Cells," *Molec. Cell. Bio.* 3:280 (1983).

Pati, "Novel vectors for expression of cDNA encoding epitope–tagged proteins in mammalian cells," *Gene* 114:285–288 (1992).

Pawson and Schlessinger, "SH2 and SH3 domains," *Current Biology* 3(7):434–442 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer et al., "Insulin Dependence of Murine Lymphoid T–Cell Leukemia," *Int. J. Cancer* 50:80–85 (1992).

Ponting, "Pleckstrin's Repeat Performance: A Novel Domain in G–protein Signaling," *TIBS* 21:245–(1996).

Posner et al., "Kinetics of Inhibition by Tyrphostins of the Tyrosine Kinase Activity of the Epidermal Growth Factor Receptor and Analysis by a New Computer Program," *Molecular Pharmacology* 45:673–683 (1994).

Pursel et al., "Genetic Engineering of Livestock," *Science* 244:1281–1288 (1989).

Redemann et al., *Mol. Cell. Biol.* 12:491–498 (1992).

Reece et al., "Pharmacokinetics of Trimetrexate Administered by Five–Day Continuous Infusion to Patients with Advanced Cancer," *Cancer Research* 47:2996–2999 (1987).

*Remington's Pharmaceutical Sciences*, 1990, 18th ed., Mack Publishing Co., Easton, PA (Table of Contents).

Rendu et al., "Inhibition of Platelet Activation by Tyrosine Kinase Inhibitors," *Biochemical Pharmacology* 44(5):881–888 (1992).

Robertson, E.J., ed., *Teratocarcinomas and Embryonic Stem Cells, A Practical Approach*, IRL Press, 1987 (Table of Contents Only).

Rubin, "Drosophila Melanogaster as an Experimental Organism" *Science* 240:1453–1459 (1988).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Molecular and Cellular Biology* 6(12):4396–4408 (1986).

Saito et al., "Molecular Characterization of Protein Tyrosine Phosphates," *Cell Growth and Diff.* 2:59–65 (1991).

Sambrook et al., *Molecular Cloning: A Laboratory Manual*, $2^{nd}$ Edition, Cold Spring Harbor Press (1989) (Table of Contents for Vol. 1, 2 and 3).

Sauro and Thomas, "Decreased Sensitivity of Aorta from Hypertensive Rats to Vasorelaxation by Tyrphostin," *Live Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Sculier et al., "Role of an Intensive Care Unit (ICU) in a Medical Onocology Department," *Cancer Immunol. and Immunotherapy* 23:A65 at abstract No. 257(1986).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–183 (1988).

Smith et al., "Single–Step Purification of Polypeptides Expressed in *Escherichia coli* as Fusions with Glutathione S–Transferase," *Gene* 67:31 (1988).

St. Groth et al., "Production of Monoclonal Antibodies: Strategy and Tactics," *J. Immunol. Methods* 35:1–21 (1980).

Stemberger et al., "The Unlabeled Antibody Enzyme Method of Immunohistochemistry," *J. Histochem. Cytochem.* 18:315 (1970).

Tijssen, "Practice and Theory of Enzyme Immunoassays," *Laboratory Techniques in Biochemistry and Molecular Biology*, Elsevier Science Publishers, Amsterdam, The Netherlands (1985).

Ulmanen et al., "Transcription and Translation of Foreign Genes in Bacillus Subtilis by the Aid of a Secretion Vector," *J. Bacteriol.* 162:176–182 (1985).

Ward et al., "Construction and Characterisation of a Series of Multi–copy Promoter–probe Plasmid Vectors for Streptomyces Using the Aminoglycoside Phosphotransferase Gene From Tn5 as Indicator," *Mol. Gen. Genet.* 203:468–478 (1986).

Weir et al., *Handbook of Experimental Immunology*, 4th Ed., Blackwell Scientific Publications, Oxford, England, Chapter 10, (1986).

Wolbring et al., "Inhibition of GTP–utilizing Enzymes by Tyrphostins," *J. Biol. Chem.* 269:22470–22472 (1994).

Yang et al., "In Vivo and In Vitro Gene Transfer to Mammalian Somatic Cells by Particle Bombardment," *Proc. Natl. Acad. Sci. USA* 87:9568–9572 (1990).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

\* cited by examiner

```
MATCH 70.5%; QRYMATCH 68.4%; MATCHES 572; CONSERVATIVE 105; MISMATCHES 121;
INDELS 13; GAPS 6;

**************   *    *****   ****  ********** **  **********
ZPEP_m       1 MDQREILQQLLKEAQKKKLNSEEFASEFLKLKRQSTKYKADKIYPTTVAQRPKNIKKNRY 60
SuPTP04_h    1 MDQREILQKFLDEAQSKKITKEEFANEFLKLKRQSTKYKADKTYPTTVAEKPKNIKKNRY 60

****** *   **********  *   **************:*********************
ZPEP_m      61 KDILPYDHSLVELSLLTSDEDSSYINASFIKGVYGPKAYIATQGPLSTTLLDFWRMIWEY 120
SuPTP04_h   61 KDILPYDYSRVELSLITSDEDSSYINANFIKGVYGPKAYIATQPLSTTLLDFWRMIWEY 120

*  .************ * *****.*********************:****** *****
ZPEP_m     121 RILVIVMACMEFEMGKKKCERYWAEPGETQLQFGPFSISCEAEKKKSDYKIRTLKAKFNN 180
SuPTP04_h  121 SVLIIVMACMEYEMGKKKKCERYWAEPGEMQLEFGPFSVSCEAEKRKSDYIIRTLKVKFNS 180

***  ****************************.*****:********:****.*****
ZPEP_m     181 ETRIIYQFHYKNWPDHDVPSSIDPILQLIWDMRCYQEDDCVPICIHCSAGCGRTGVICAV 240
SuPTP04_h  181 ETRTIYQFHYKNWPDHDVPSSIDPILELIWDVRCYQEDDSVPICIHCSAGCGRTGVICAI 240

************ ****************..*******  ***** **:************
ZPEP_m     241 DYTWMLLKDGIIPKNFSVFNLIQEMRTQRPSLVQTQEQYELVYSAVLELFKRHMDVISDN 300
SuPTP04_h  241 DYTWMLLKDGIIPENFSVFSLIREMRTQRPSLVQTQEQYELVYNAVLELFKRQMDVIRDK 300
```

FIG. 1 (CONT.)-1

```
ZPEP_m    301 HLGREIQAQCSIPEQSLTVEADSCPLDLPKNAMRDVKTTNQHSKQGAEAESTGGSSLGLR 360
SuPTP04_h 301 HSGTESQAKHCIPEKNHTLQADSYSPNLPKSTTKAAKMMNQQR---TKMEIKESSSFDFR 357

ZPEP_m    361 TSTMNAEEELVLHSAKSSPSFNCLELNCGCNNKAVITRNGQARASPVVGEPLQKYQSLDF 420
SuPTP04_h 358 TSEISAKEELVLHPAKSSTSFDFLELNYSFDKNADTTMKWQTKAFPIVGEPLQKHQSLDL 417

ZPEP_m    421 GSMLFGSCPSALPINTADRYHNSKGPVKRTKSTPFELIQQRKTNDLAVGDGFSCLESQLH 480
SuPTP04_h 418 GSLLFEGCSNSKPVNAAGRYFNSKVPITRTKSTPFELIQQRETKEVDSKENFSYLESQPH 477

ZPEP_m    481 EHYSLRELQVQRVAHVSSEELNYSLPGAC-----DASCVPRHSPGALRVHLYTSLAEDPY 535
SuPTP04_h 478 DSCFV-EMQAQKVMHVSSAELNYSLPYDSKHQIRNASNVKHHDSSALGVYSYIPLVENPY 536

ZPEP_m    536 FSSSPPPNSADSKMSFDLPEKQDGATSPGALLPASSTTSFFYSNPHDSLVMNTLTSFSPPL 595
SuPTP04_h 537 FSSWPPSGTSSKMSLDLPEKQDGTVFPSSLLPTSSTSLFSYYNSHDSLSLNSPTNISSLL 596

ZPEP_m    596 NQETAVEAPSRRTDDEIPPLPERTPESFIVVEEAGEPSPRVTESLP--LVVTFGASPEC 653
SuPTP04_h 597 NQESAVLATAPRIDDEIPPPLPVRTPESFIVVEEAGEFSPNVPKSLSSAVKVKIGTSLEW 656
```

*FIG. 1 (CONT.)-2*

```
ZPEP_m     654 ........*.*...***.........*.****.*..***.*****************.*****************
SuPTP04_h  657 SQTSE-MKSHDSVGFTPSKNVKLRSPKSDRHQD-GSPPPPLPERTLESFFLADEDCIQAQ 711
               GGTSEPKKFDDSVILRPSKSVKLRSPKSELHQDRSSPPPPLPERTLESFFLADEDCMQAQ 716

ZPEP_m     712 ..:..*.******.*****.*****.***********.**.*****.***.*.**.*.**
SuPTP04_h  717 AVQTSSTSYPETTENSTSSKQTLRTPGKSFTRSKSLKIFRNMKKSVCNSSSPSKPTERVQ 771
               SIETYSTSYPDTMENSTSSKQTLKTPGKSFTRSKSLKILRNMKKSICNSCPPNKPAESVQ 776

ZPEP_m     772 .*************.*************..*.
SuPTP04_h  777 PKNSSSFLNFGFGNRFSKPKGPRNPPSAWNM 802
               SNNSSSFLNFGFANRFSKPKGPRNPPPTWNI 807
```

*FIG. 1 (CONT.)-3*

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH:         3580 base pairs
      (B) TYPE:           nucleic acid
      (C) STRANDEDNESS:  single
      (D) TOPOLOGY:      linear (xi) SEQUENCE DESCRIPTION: SEQ ID NO: 1:

```
CCCGGGTGCC CTCCCTCAAC CTACTTATAG ACTATTTTTC TTGCTCTGCA GCATGGACCA      60

AAGAGAAATT CTGCAGAAGT TCCTGGATGA GGCCCAAAGC AAGAAAATTA CTAAAGAGGA     120

GTTTGCCAAT GAATTTCTGA AGCTGAAAAG GCAATCTACC AAGTACAAGG CAGACAAAAC     180

CTATCCTACA ACTGTGGCTG AGAAGCCCAA GAATATCAAG AAAAACAGAT ATAAGGATAT     240

TTTGCCCTAT GATTATAGCC GGGTAGAACT ATCCCTGATA ACCTCTGATG AGGATTCCAG     300

CTACATCAAT GCCAACTTCA TTAAGGGAGT TTATGGACCC AAGGCTTATA TTGCCACCCA     360

GGGTCCTTTA TCTACAACCC TCCTGGACTT CTGGAGGATG ATTTGGGAAT ATAGTGTCCT     420

TATCATTGTT ATGGCATGCA TGGAGTATGA AATGGGAAAG AAAAAGTGTG AGCGCTACTG     480

GGCTGAGCCA GGAGAGATGC AGCTGGAATT TGGCCCTTTC TCTGTATCCT GTGAAGCTGA     540

AAAAAGGAAA TCTGATTATA TAATCAGGAC TCTAAAAGTT AAGTTCAATA GTGAAACTCG     600

AACTATCTAC CAGTTTCATT ACAAGAATTG GCCAGACCAT GATGTACCTT CATCTATAGA     660

CCCTATTCTT GAGCTCATCT GGGATGTACG TTGTTACCAA GAGGATGACA GTGTTCCCAT     720

ATGCATTCAC TGCAGTGCTG GCTGTGGAAG GACTGGTGTT ATTTGTGCTA TTGATTATAC     780

ATGGATGTTG CTAAAAGATG GGATAATTCC TGAGAACTTC AGTGTTTTCA GTTTGATCCG     840

GGAAATGCGG ACACAGAGGC CTTCATTAGT TCAAACGCAG GAACAATATG AACTGGTCTA     900

CAATGCTGTA TTAGAACTAT TTAAGAGACA GATGGATGTT ATCAGAGATA AACATTCTGG     960

AACAGAGAGT CAAGCAAAGC ATTGTATTCC TGAGAAAAAT CACACTCTCC AAGCAGACTC    1020

TTATTCTCCT AATTTACCAA AAAGTACCAC AAAAGCAGCA AAAATGATGA ACCAACAAAG    1080
```

```
GACAAAAATG GAAATCAAAG AATCTTCTTC CTTTGACTTT AGGACTTCTG AAATAAGTGC    1140

AAAAGAAGAG CTAGTTTTGC ACCCTGCTAA ATCAAGCACT TCTTTTGACT TTCTGGAGCT    1200

AAATTACAGT TTTGACAAAA ATGCTGACAC AACCATGAAA TGGCAGACAA AGGCATTTCC    1260

AATAGTTGGG GAGCCTCTTC AGAAGCATCA AAGTTTGGAT TTGGGCTCTC TTTTGTTTGA    1320

GGGATGTTCA AATTCTAAAC CTGTAAATGC AGCAGGAAGA TATTTTAATT CAAAGGTGCC    1380

AATAACACGG ACCAAATCAA CTCCTTTTGA ATTGATACAG CAGAGAGAAA CCAAGGAGGT    1440

GGACAGCAAG GAAAACTTTT CTTATTTGGA ATCTCAACCA CATGATTCTT GTTTTGTAGA    1500

GATGCAGGCT CAAAAAGTAA TGCATGTTTC TTCAGCAGAA CTGAATTATT CACTGCCATA    1560

TGACTCTAAA CACCAAATAC GTAATGCCTC TAATGTAAAG CACCATGACT CTAGTGCTCT    1620

TGGTGTATAT TCTTACATAC CTTTAGTGGA AAATCCTTAT TTTTCATCAT GGCCTCCAAG    1680

TGGTACCAGT TCTAAGATGT CTCTTGATTT ACCTGAGAAG CAAGATGGAA CTGTTTTTCC    1740

TTCTTCTCTG TTGCCAACAT CCTCTACATC CCTCTTCTCT TATTACAATT CACATGATTC    1800

TTTATCACTG AATTCTCCAA CCAATATTTC CTCACTATTG AACCAGGAGT CAGCTGTACT    1860

AGCAACTGCT CCAAGGATAG ATGATGAAAT CCCCCCTCCA CTTCCTGTAC GGACACCTGA    1920

ATCATTTATT GTGGTTGAGG AAGCTGGAGA ATTCTCACCA AATGTTCCCA AATCCTTATC    1980

CTCAGCTGTG AAGGTAAAAA TTGGAACATC ACTGGAATGG GGTGGAACAT CTGAACCAAA    2040

GAAATTTGAT GACTCTGTGA TACTTAGACC AAGCAAGAGT GTAAAACTCC GAAGTCCTAA    2100

ATCAGAACTA CATCAAGATC GTTCTTCTCC CCCACCTCCT CTCCCAGAAA GAACTCTAGA    2160

GTCCTTCTTT CTTGCCGATG AAGATTGTAT GCAGGCCCAA TCTATAGAAA CATATTCTAC    2220

TAGCTATCCT GACACCATGG AAAATTCAAC ATCTTCAAAA CAGACACTGA AGACTCCTGG    2280

AAAAAGTTTC ACAAGGAGTA AGAGTTTGAA AATTTTGCGA ACATGAAAA AGAGTATCTG     2340

TAATTCTTGC CCACCAAACA AGCCTGCAGA ATCTGTTCAG TCAAATAACT CCAGCTCATT    2400

TCTGAATTTT GGTTTTGCAA ACCGTTTTTC AAAACCCAAA GGACCAAGGA ATCCACCACC    2460

AACTTGGAAT ATTTAATAAA ACTCCAGATT TATAATAATA TGGGCTGCAA GTACACCTGC    2520

AAATAAAACT ACTAGAATAC TGCTAGTTAA AATAAGTGCT CTATATGCAT AATATCAAAT    2580

ATGAAGATAT GCTAATGTGT TAATAGCTTT TAAAAGAAAA GCAAAATGCC AATAAGTGCC    2640

AGTTTTGCAT TTTCATATCA TTTGCATTGA GTTGAAAACT GCAAATAAAA GTTTGTCACT    2700

TGAGCTTATG TACAGAATGC TATATGAGAA ACACTTTTAG AATGGATTTA TTTTTCATTT    2760

TTGCCAGTTA TTTTTATTTT CTTTTACTTT TTTACATAAA CATAAACTTC AAAAGGTTTG    2820

TAAGATTTGG ATCTCAACTA ATTTCTACAT TGCCAGAATA TACTATAAAA AGTTAAAAAA    2880

AAACTTACTT TGTGGGTTGC AATACAAACT GCTCTTGACA ATGACTATTC CCTGACAGTT    2940

ATTTTTGCCT AAATGGAGTA TACCTTGTAA ATCTTCCCAA ATGTTGTGGA AAACTGGAAT    3000

ATTAAGAAAA TGAGAAATTA TATTTATTAG AATAAAATGT GCAAATAATG ACAATTATTT    3060

GAATGTAACA AGGAATTCAA CTGAAATCCT GATAAGTTTT AACCAAAGTC ATTAAATTAC    3120

CAATTCTAGA AAAGTAATCA ATGAAATATA ATAGCTATCT TTTGGTAGCA AAAGATATAA    3180

ATTGTATATG TTTATACAGG ATCTTTCAGA TCATGTGCAA TTTTTATCTA ACCAATCAGA    3240

AATACTAGTT TAAAATGAAT TTCTATATGA ATATGGATCT GCCATAAGAA AATCTAGTTC    3300

AACTCTAATT TTATGTAGTA AATAAATTGG CAGGTAATTG TTTTTACAAA GAATCCACCT    3360

GACTTCCCCT AATGCATTAA AAATATTTTT ATTTAAATAA CTTTATTTAT AACTTTTAGA    3420

AACATGTAGT ATTGTTTAAA CATCATTTGT TCTTCAGTAT TTTTCATTTG GAAGTCCAAT    3480
```

```
AGGGCAAATT GAATGAAGTA TTATTATCTG TCTCTTGTAG TACAATGTAT CCAACAGACA    3540

CTCAATAAAC TTTTTGGTTG TTAAAAAAAA AAAAAAAAA                           3580

(2) INFORMATION FOR SEQ ID NO: 2:

(i) SEQUENCE CHARACTERISTICS:
        (A) LENGTH:         807 amino acids
        (B) TYPE:           amino acid
        (C) STRANDEDNESS:   single
        (D) TOPOLOGY:       linear (ii) MOLECULE TYPE:             peptide (xi) SEQUENCE DESCRIPTION: SEQ ID NO: 2:

Met Asp Gln Arg Glu Ile Leu Gln Lys Phe Leu Asp Glu Ala Gln Ser
 1               5                  10                  15

Lys Lys Ile Thr Lys Glu Glu Phe Ala Asn Glu Phe Leu Lys Leu Lys
            20                  25                  30

Arg Gln Ser Thr Lys Tyr Lys Ala Asp Lys Thr Tyr Pro Thr Thr Val
        35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110

Phe Trp Arg Met Ile Trp Glu Tyr Ser Val Leu Ile Ile Val Met Ala
        115                 120                 125

Cys Met Glu Tyr Glu Met Gly Lys Lys Lys Cys Glu Arg Tyr Trp Ala
    130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
            180                 185                 190

Trp Pro Asp His Asp Val Pro Ser Ser Ile Asp Pro Ile Leu Glu Leu
        195                 200                 205

Ile Trp Asp Val Arg Cys Tyr Gln Glu Asp Asp Ser Val Pro Ile Cys
    210                 215                 220

Ile His Cys Ser Ala Gly Cys Gly Arg Thr Gly Val Ile Cys Ala Ile
225                 230                 235                 240

Asp Tyr Thr Trp Met Leu Leu Lys Asp Gly Ile Ile Pro Glu Asn Phe
                245                 250                 255

Ser Val Phe Ser Leu Ile Arg Glu Met Arg Thr Gln Arg Pro Ser Leu
            260                 265                 270

Val Gln Thr Gln Glu Gln Tyr Glu Leu Val Tyr Asn Ala Val Leu Glu
        275                 280                 285

Leu Phe Lys Arg Gln Met Asp Val Ile Arg Asp Lys His Ser Gly Thr
    290                 295                 300

Glu Ser Gln Ala Lys His Cys Ile Pro Glu Lys Asn His Thr Leu Gln
305                 310                 315                 320

Ala Asp Ser Tyr Ser Pro Asn Leu Pro Lys Ser Thr Thr Lys Ala Ala
```

-continued

```
              325                 330                 335
Lys Met Met Asn Gln Gln Arg Thr Lys Met Glu Ile Lys Glu Ser Ser
                340                 345                 350

Ser Phe Asp Phe Arg Thr Ser Glu Ile Ser Ala Lys Glu Glu Leu Val
                355                 360                 365

Leu His Pro Ala Lys Ser Ser Thr Ser Phe Asp Phe Leu Glu Leu Asn
                370                 375                 380

Tyr Ser Phe Asp Lys Asn Ala Asp Thr Thr Met Lys Trp Gln Thr Lys
385                 390                 395                 400

Ala Phe Pro Ile Val Gly Glu Pro Leu Gln Lys His Gln Ser Leu Asp
                405                 410                 415

Leu Gly Ser Leu Leu Phe Glu Gly Cys Ser Asn Ser Lys Pro Val Asn
                420                 425                 430

Ala Ala Gly Arg Tyr Phe Asn Ser Lys Val Pro Ile Thr Arg Thr Lys
                435                 440                 445

Ser Thr Pro Phe Glu Leu Ile Gln Gln Arg Glu Thr Lys Glu Val Asp
                450                 455                 460

Ser Lys Glu Asn Phe Ser Tyr Leu Glu Ser Gln Pro His Asp Ser Cys
465                 470                 475                 480

Phe Val Glu Met Gln Ala Gln Lys Val Met His Val Ser Ser Ala Glu
                485                 490                 495

Leu Asn Tyr Ser Leu Pro Tyr Asp Ser Lys His Gln Ile Arg Asn Ala
                500                 505                 510

Ser Asn Val Lys His His Asp Ser Ser Ala Leu Gly Val Tyr Ser Tyr
                515                 520                 525

Ile Pro Leu Val Glu Asn Pro Tyr Phe Ser Ser Trp Pro Pro Ser Gly
                530                 535                 540

Thr Ser Ser Lys Met Ser Leu Asp Leu Pro Glu Lys Gln Asp Gly Thr
545                 550                 555                 560

Val Phe Pro Ser Ser Leu Leu Pro Thr Ser Ser Thr Ser Leu Phe Ser
                565                 570                 575 yr Tyr Asn Ser His Asp Ser Leu Ser Leu Asn Ser Pro Thr Asn Ile
                580                 585                 590

Ser Ser Leu Leu Asn Gln Glu Ser Ala Val Leu Ala Thr Ala Pro Arg
                595                 600                 605

Ile Asp Asp Glu Ile Pro Pro Leu Pro Val Arg Thr Pro Glu Ser
                610                 615                 620

Phe Ile Val Val Glu Glu Ala Gly Glu Phe Ser Pro Asn Val Pro Lys
625                 630                 635                 640

Ser Leu Ser Ser Ala Val Lys Val Lys Ile Gly Thr Ser Leu Glu Trp
                645                 650                 655

Gly Gly Thr Ser Glu Pro Lys Lys Phe Asp Asp Ser Val Ile Leu Arg
                660                 665                 670

Pro Ser Lys Ser Val Lys Leu Arg Ser Pro Lys Ser Glu Leu His Gln
                675                 680                 685

Asp Arg Ser Ser Pro Pro Pro Leu Pro Glu Arg Thr Leu Glu Ser
                690                 695                 700

Phe Phe Leu Ala Asp Glu Asp Cys Met Gln Ala Gln Ser Ile Glu Thr
705                 710                 715                 720

Tyr Ser Thr Ser Tyr Pro Asp Thr Met Glu Asn Ser Thr Ser Ser Lys
                725                 730                 735

Gln Thr Leu Lys Thr Pro Gly Lys Ser Phe Thr Arg Ser Lys Ser Leu
                740                 745                 750
```

```
Lys Ile Leu Arg Asn Met Lys Lys Ser Ile Cys Asn Ser Cys Pro Pro
        755                 760                 765
Asn Lys Pro Ala Glu Ser Val Gln Ser Asn Asn Ser Ser Ser Phe Leu
    770                 775                 780
Asn Phe Gly Phe Ala Asn Arg Phe Ser Lys Pro Lys Gly Pro Arg Asn
785                 790                 795                 800
Pro Pro Pro Thr Trp Asn Ile
            805
```

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: The letter "Y" stands for C or T.
            The letter "V" stands for A, C or G.
            The letter "R" stands for A or G.
            The letter "N" stands for A, C, G or T.

(xi) SEQUENCE DESCRIPTION: SEQ ID NO: 3:

GAYTTYTGGV RNATGRTNTG GGA                23

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: The letter "S" stands for C or G.
            The letter "Y" stands for C or T.
            The letter "N" stands for A, C, G or T.
            The letter "W" stands for A or T.
            The letter "R" stands for A or G.

(xi) SEQUENCE DESCRIPTION: SEQ ID NO: 4:

CGGCCSAYNC CNGCNSWRCA RTG                23

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: "Xaa" in positions 4 and 6 stand for an unspecified amino acid.
            "Xaa" in position 8 stands for either Glu or Asp.

(xi) SEQUENCE DESCRIPTION: SEQ ID NO: 5:

```
Asp Phe Trp Xaa Met Xaa Trp Xaa
 1               5
```

(2) INFORMATION FOR SEQ ID NO: 6:

```
        (i) SEQUENCE CHARACTERISTICS:
            (A) LENGTH:           7 amino acids
            (B) TYPE:             amino acid
            (C) STRANDEDNESS:     single
            (D) TOPOLOGY:         liear (ii) MOLECULE TYPE:        peptide (ix) FEATURE:
            (D) OTHER INFORMATION:   "Xaa" in positions 3 and 6 stand
                 for an unspecified amino acid.

(xi) SEQUENCE DESCRIPTION: SEQ ID NO: 6:

His Cys Xaa Ala Gly Xaa Gly
 1               5

(2) INFORMATION FOR SEQ ID NO: 7:

(i) SEQUENCE CHARACTERISTICS:
            (A) LENGTH:           34 base pairs
            (B) TYPE:             nucleic acid
            (C) STRANDEDNESS:     single
            (D) TOPOLOGY:         linear (xi) SEQUENCE DESCRIPTION: SEQ ID NO: 7:

CACCGTTCGA GTATTTCAGA TTGTGAAGAA GTCC                               34

(2) INFORMATION FOR SEQ ID NO: 8:

(i) SEQUENCE CHARACTERISTICS:
            (A) LENGTH:           34 base pairs
            (B) TYPE:             nucleic acid
            (C) STRANDEDNESS:     single
            (D) TOPOLOGY:         linear (xi) SEQUENCE DESCRIPTION: SEQ ID NO: 8:

GGACTTCTTC ACAATCTGAA ATACTCGAAC GGTG                               34

(2) INFORMATION FOR SEQ ID NO: 9:

(i) SEQUENCE CHARACTERISTICS:
            (A) LENGTH:           33 base pairs
            (B) TYPE:             nucleic acid
            (C) STRANDEDNESS:     single
            (D) TOPOLOGY:         linear (xi) SEQUENCE DESCRIPTION: SEQ ID NO: 9:

CCGTTATGTG AGGAAGAGCC ACATTACAGG ACC                                33

(2) INFORMATION FOR SEQ ID NO: 10:

(i) SEQUENCE CHARACTERISTICS:
            (A) LENGTH:           33 base pairs
            (B) TYPE:             nucleic acid
            (C) STRANDEDNESS:     single
            (D) TOPOLOGY:         linear (xi) SEQUENCE DESCRIPTION: SEQ ID NO: 10:

GGTCCTGTAA TGTGGCTCTT CCTCACATAA CGG                                33

(2) INFORMATION FOR SEQ ID NO: 11:

(i) SEQUENCE CHARACTERISTICS:
            (A) LENGTH:           23 base pairs
            (B) TYPE:             nucleic acid
            (C) STRANDEDNESS:     single
            (D) TOPOLOGY:         linear
```

```
    (xi) SEQUENCE DESCRIPTION: SEQ ID NO: 11:

GGCATGCATG GAGTATGAAA TGG                                              23

(2) INFORMATION FOR SEQ ID NO: 12:

(i) SEQUENCE CHARACTERISTICS:
        (A) LENGTH:           30 base pairs
        (B) TYPE:             nucleic acid
        (C) STRANDEDNESS:     single
        (D) TOPOLOGY:         linear (xi) SEQUENCE DESCRIPTION: SEQ ID NO: 12:

CGTACATCCC AGATGAGCTC AAGAATAGGG                                       30

(2) INFORMATION FOR SEQ ID NO: 13:

(i) SEQUENCE CHARACTERISTICS:
        (A) LENGTH:           10 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 13:

Tyr Pro Tyr Asp Val Pro Asp Tyr Ala Ser
 1               5                   10

(2) INFORMATION FOR SEQ ID NO: 14:

(i) SEQUENCE CHARACTERISTICS:
        (A) LENGTH:           5 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 14:

His Cys Ser Ala Gly
 1               5

(2) INFORMATION FOR SEQ ID NO: 15:

(i) SEQUENCE CHARACTERISTICS:
        (A) LENGTH:           31 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 15:

Ser Trp Pro Pro Ser Gly Thr Ser Ser Lys Met Ser Leu Asp Leu
 1               5                   10                  15

Pro Glu Lys Gln Asp Gly Thr Val Phe Pro Ser Ser Leu Leu Pro
                20                  25                  30

(2) INFORMATION FOR SEQ ID NO: 16:

(i) SEQUENCE CHARACTERISTICS:
        (A) LENGTH:           30 amino acids
        (B) TYPE:             amino acid
        (C) STRANDEDNESS:     single
        (D) TOPOLOGY:         linear (ii) MOLECULE TYPE:       peptide
```

```
       (xi) SEQUENCE DESCRIPTION: SEQ ID NO: 16:

Tyr Ser Leu Pro Tyr Asp Ser Lys His Gln Ile Arg Asn Ala Ser Asn
 1               5                  10                  15

Val Lys His His Asp Ser Ser Ala Leu Gly Val Tyr Ser Tyr
            20                  25                  30

(2) INFORMATION FOR SEQ ID NO: 17:

(i) SEQUENCE CHARACTERISTICS:
           (A) LENGTH:           30 amino acids
           (B) TYPE:             amino acid
           (C) STRANDEDNESS:     single
           (D) TOPOLOGY:         linear (ii) MOLECULE TYPE:         peptide (xi) SEQUENCE DESCRIPTION: SEQ ID NO: 17:

His Thr Leu Gln Ala Asp Ser Tyr Ser Pro Asn Leu Pro Lys Ser Thr
 1               5                  10                  15

Thr Lys Ala Ala Lys Met Met Asn Gln Gln Arg Thr Lys Cys
            20                  25                  30

(2) INFORMATION FOR SEQ ID NO: 18:

(i) SEQUENCE CHARACTERISTICS:
           (A) LENGTH:           802 amino acids
           (B) TYPE:             amino acid
           (C) STRANDEDNESS:     single
           (D) TOPOLOGY:         linear (ii) MOLECULE TYPE:         peptide (xi) SEQUENCE DESCRIPTION: SEQ ID NO: 18:

Met Asp Gln Arg Glu Ile Leu Gln Gln Leu Leu Lys Glu Ala Gln Lys
 1               5                  10                  15

Lys Lys Leu Asn Ser Glu Glu Phe Ala Ser Glu Phe Leu Lys Leu Lys
            20                  25                  30

Arg Gln Ser Thr Lys Tyr Lys Ala Asp Lys Ile Tyr Pro Thr Thr Val
            35                  40                  45

Ala Gln Arg Pro Lys Asn Ile Lys Lys Asn Arg Tyr Lys Asp Ile Leu
50                       55                  60

Pro Tyr Asp His Ser Leu Val Glu Leu Ser Leu Leu Thr Ser Asp Glu
65                       70                  75                  80

Asp Ser Ser Tyr Ile Asn Ala Ser Phe Ile Lys Gly Val Tyr Gly Pro
                85                  90                  95

Lys Ala Tyr Ile Ala Thr Gln Gly Pro Leu Ser Thr Thr Leu Leu Asp
                100                 105                 110

Phe Trp Arg Met Ile Trp Glu Tyr Arg Ile Leu Val Ile Val Met Ala
                115                 120                 125

Cys Met Glu Phe Glu Met Gly Lys Lys Lys Cys Glu Arg Tyr Trp Ala
130                 135                 140

Glu Pro Gly Glu Thr Gln Leu Gln Phe Gly Pro Phe Ser Ile Ser Cys
145                 150                 155                 160

Glu Ala Glu Lys Lys Lys Ser Asp Tyr Lys Ile Arg Thr Leu Lys Ala
                165                 170                 175

Lys Phe Asn Asn Glu Thr Arg Ile Ile Tyr Gln Phe His Tyr Lys Asn
                180                 185                 190

Trp Pro Asp His Asp Val Pro Ser Ser Ile Asp Pro Ile Leu Gln Leu
                195                 200                 205
```

```
Ile Trp Asp Met Arg Cys Tyr Gln Glu Asp Cys Val Pro Ile Cys
210                 215                 220

Ile His Cys Ser Ala Gly Cys Gly Arg Thr Gly Val Ile Cys Ala Val
225             230                 235                 240

Asp Tyr Thr Trp Met Leu Leu Lys Asp Gly Ile Ile Pro Lys Asn Phe
                245                 250                 255

Ser Val Phe Asn Leu Ile Gln Glu Met Arg Thr Gln Arg Pro Ser Leu
            260                 265                 270

Val Gln Thr Gln Glu Gln Tyr Glu Leu Val Tyr Ser Ala Val Leu Glu
        275                 280                 285

Leu Phe Lys Arg His Met Asp Val Ile Ser Asp Asn His Leu Gly Arg
290                 295                 300

Glu Ile Gln Ala Gln Cys Ser Ile Pro Glu Gln Ser Leu Thr Val Glu
305                 310                 315                 320

Ala Asp Ser Cys Pro Leu Asp Leu Pro Lys Asn Ala Met Arg Asp Val
                325                 330                 335

Lys Thr Thr Asn Gln His Ser Lys Gln Gly Ala Glu Ala Glu Ser Thr
            340                 345                 350

Gly Gly Ser Ser Leu Gly Leu Arg Thr Ser Thr Met Asn Ala Glu Glu
        355                 360                 365

Glu Leu Val Leu His Ser Ala Lys Ser Ser Pro Ser Phe Asn Cys Leu
370                 375                 380

Glu Leu Asn Cys Gly Cys Asn Asn Lys Ala Val Ile Thr Arg Asn Gly
385                 390                 395                 400

Gln Ala Arg Ala Ser Pro Val Val Gly Glu Pro Leu Gln Lys Tyr Gln
                405                 410                 415

Ser Leu Asp Phe Gly Ser Met Leu Phe Gly Ser Cys Pro Ser Ala Leu
            420                 425                 430

Pro Ile Asn Thr Ala Asp Arg Tyr His Asn Ser Lys Gly Pro Val Lys
        435                 440                 445

Arg Thr Lys Ser Thr Pro Phe Glu Leu Ile Gln Gln Arg Lys Thr Asn
450                 455                 460

Asp Leu Ala Val Gly Asp Gly Phe Ser Cys Leu Glu Ser Gln Leu His
465                 470                 475                 480

Glu His Tyr Ser Leu Arg Glu Leu Gln Val Gln Arg Val Ala His Val
                485                 490                 495

Ser Ser Glu Glu Leu Asn Tyr Ser Leu Pro Gly Ala Cys Asp Ala Ser
            500                 505                 510

Cys Val Pro Arg His Ser Pro Gly Ala Leu Arg Val His Leu Tyr Thr
        515                 520                 525

Ser Leu Ala Glu Asp Pro Tyr Phe Ser Ser Ser Pro Asn Ser Ala
530                 535                 540

Asp Ser Lys Met Ser Phe Asp Leu Pro Glu Lys Gln Asp Gly Ala Thr
545                 550                 555                 560

Ser Pro Gly Ala Leu Leu Pro Ala Ser Ser Thr Thr Ser Phe Phe Tyr
                565                 570                 575

Ser Asn Pro His Asp Ser Leu Val Met Asn Thr Leu Thr Ser Phe Ser
            580                 585                 590

Pro Pro Leu Asn Gln Glu Thr Ala Val Glu Ala Pro Ser Arg Arg Thr
        595                 600                 605

Asp Asp Glu Ile Pro Pro Leu Pro Glu Arg Thr Pro Glu Ser Phe
610                 615                 620

Ile Val Val Glu Glu Ala Gly Glu Pro Ser Pro Arg Val Thr Glu Ser
```

```
                 625                     630                     635                     640
Leu Pro Leu Val Val Thr Phe Gly Ala Ser Pro Glu Cys Ser Gly Thr
                645                     650                     655

Ser Glu Met Lys Ser His Asp Ser Val Gly Phe Thr Pro Ser Lys Asn
            660                     665                     670

Val Lys Leu Arg Ser Pro Lys Ser Asp Arg His Gln Asp Gly Ser Pro
            675                     680                     685

Pro Pro Pro Leu Pro Glu Arg Thr Leu Glu Ser Phe Phe Leu Ala Asp
        690                     695                     700

Glu Asp Cys Ile Gln Ala Gln Ala Val Gln Thr Ser Ser Thr Ser Tyr
705                     710                     715                     720

Pro Glu Thr Thr Glu Asn Ser Thr Ser Ser Lys Gln Thr Leu Arg Thr
                725                     730                     735

Pro Gly Lys Ser Phe Thr Arg Ser Lys Ser Leu Lys Ile Phe Arg Asn
                740                     745                     750

Met Lys Lys Ser Val Cys Asn Ser Ser Ser Pro Ser Lys Pro Thr Glu
            755                     760                     765

Arg Val Gln Pro Lys Asn Ser Ser Phe Leu Asn Phe Gly Phe Gly
        770                     775                     780

Asn Arg Phe Ser Lys Pro Lys Gly Pro Arg Asn Pro Pro Ser Ala Trp
785                     790                     795                     800

Asn Met
```

DIAGNOSIS AND TREATMENT OF PTP04 RELATED DISORDERS

RELATED APPLICATIONS

This application claims priority to the U.S. Provisional Patent Application No. 60/047,222, by Jallal et al., entitled "Diagnosis and Treatment of PTP04 Related Disorders," and filed May 20, 1997, which is incorporated herein by reference in its entirety, including any drawings.

FIELD OF THE INVENTION

The present invention relates to tyrosine phosphatases. In particular, the invention concerns a protein we have named PTP04, nucleotide sequences encoding PTP04, various products and assay methods that can be used for identifying compounds useful for the diagnosis and treatment of various PTP04-related diseases and conditions, for example cell proliferative disorders.

BACKGROUND OF THE INVENTION

The following description is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function. The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines.

The phosphorylation state of a given substrate is also regulated by a class of proteins responsible for removal of the phosphate group added to a given substrate by a protein kinase. The protein phosphatases can also be classified as being specific for either serine/threonine or tyrosine. The known enzymes can be divided into two groups—receptor and non-receptor type proteins. Most receptor-type protein tyrosine phosphatases (RPTPs) contain two conserved catalytic tyrosine phosphatase domains each of which encompasses a segment of 240 amino acid residues (Saito et al, *Cell Growth and Diff.* 2:59–65, 1991). The RPTPs can be subclassified further based upon the amino acid sequence diversity of their extracellular domains (Saito, et al, supra; Krueger, et al, *Proc. Natl. Acad. Sci. USA* 89:7417–7421, 1992). Alignment of primary peptide sequences of both types of known PTPases shows some sequence consensus in catalytic domains and has made it possible to identify cDNAs encoding proteins with tyrosine phosphate activity via the polymerase chain reaction (PCR).

Many kinases and phosphatases are involved in regulatory cascades wherein their substrates may include other kinases and phosphatases whose activities are regulated by their phosphorylation state. Ultimately the activity of some downstream effector is modulated by phosphorylation resulting from activation of such a pathway.

Tyrosine phosphatases have been thought to be possible candidate cancer causing proteins. Inappropriate activity through overexpression of RPTP-alpha, for example, has been associated with colon cancer (Pallen, et al, WO 94/01119, published Jan. 20, 1994). A need exists to identify additional proteins whose inappropriate activity may lead to cancer or other disorders so that pharmaceutical compounds for the treatment of those disorders might also be identified.

SUMMARY OF THE INVENTION

The present invention concerns PTP04 polypeptides, nucleic acids encoding such polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding a PTP04 polypeptide.

By "isolated" in reference to nucleic acid is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of non-nucleotide material naturally associated with it and thus is meant to be distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. The term is also chosen to distinguish clones already in existence which may encode PTP04 but which have not been isolated from other clones in a library of clones. Thus, the term covers clones encoding PTP04 which are isolated from other non-PTP04 clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybrydization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples below. High stringent conditions may mean conditions that are at least as stringent as the following: hybridization in 50% formamide, 5×SSC, 50 mM $NaH_3PO_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

A PTP04 polypeptide can be encoded by a full-length nucleic acid sequence or any portion of the full-length nucleic acid sequence. In preferred embodiments the isolated nucleic acid comprises, consists essentially of, or consists of a nucleic acid sequence set forth in SEQ ID NO:1, a nucleic acid sequence that hybridizes to the nucleic acid sequence set forth in SEQ ID NO:1 or a functional derivative (as defined below) of either. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

The term "mammalian" refers to such organisms as mice, rats, rabbits, goats, more preferably monkeys and apes, and most preferably humans.

In other preferred embodiments, the nucleic acid molecule of the invention comprises a nucleotide sequence that (a) encodes a polypeptide having the full length amino acid sequence set forth in SEQ ID NO:2; (b) is the complement of the nucleotide sequence of (a); (c) hybridizes under highly stringent conditions to the nucleotide molecule of (a) and encodes a naturally occurring PTP04 polypeptide; (d) encodes a PTP04 polypeptide having the full length amino acid sequence of the sequence set forth in SEQ ID NO:2, except that it lacks one or more of the following segments of amino acid residues: 1–48, 49–294, 295–807 of SEQ ID NO:2; (e) is the complement of the nucleotide sequence of (d); (f) encodes a polypeptide having the amino acid sequence set forth in SEQ ID NO:2 from amino acid residues 1–48, 49–294, 295–807 of SEQ ID NO:2; (g) is the complement of the nucleotide sequence of (f); (h) encodes a polypeptide having the full length amino acid sequence set forth in SEQ ID NO:2, except that it lacks one or more of the domains selected from the group consisting of a signal peptide, an extracellular region, a transmembrane domain, a cytoplasmic domain, and a catalytic domain; or (i) is the complement of the nucleotide sequence of (h). The nucleic acid molecule of the invention is isolated, enriched, or purified from, preferably, a mammal, or most preferably from a human.

In yet other preferred embodiments the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions", it is meant regions present on two or more nucleic acids encoding a PTP04 polypeptide, to which a particular nucleic acid sequence can hybridize under lower stringency conditions. Examples of lower stringency conditions suitable for screening for nucleic acids encoding PTP04 polypeptides are provided in Abe, et al. *J. Biol. Chem.* 19:13361 (1992) (hereby incorporated by reference herein in its entirety, including any drawings). Preferably, conserved regions differ by no more than 5 out of 20 continguous nucleotides.

By "unique nucleic acid region" it is meant a sequence present in a full length nucleic acid coding for a PTP04 polypeptide that is not present in a sequence coding for any other known naturally occurring polypeptide. Such regions preferably comprise 14, 17, 21 or more contiguous nucleotides present in the full length nucleic acid encoding a PTP04 polypeptide. In particular, a unique nucleic acid region is preferably of human origin.

In yet another aspect, the invention relates to a nucleic acid vector comprising a nucleic acid molecule encoding a PTP04 polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the PTP04 nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the PTP04 nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding a PTP04 polypeptide in a sample.

The term "nucleic acid probe" refers to a nucleic molecule that is complementary to and can bind a nucleic acid sequence encoding the amino acid sequence substantially similar to that set forth in SEQ ID NO:2.

The nucleic acid probe contains nucleic acid that will hybridize specifically to a sequence of at least 14, preferably 17, 20 or 22, contiguous nucleotides set forth in SEQ ID NO:1 or a functional derivative thereof. The probe is preferably at least 14, 17 or more bases in length and selected to hybridize specifically to a unique region of a PTP04 endocing nucleic acid.

In preferred embodiments the nucleic acid probe hybridizes to nucleic acid encoding at least 14 contiguous amino acids of the full-length sequence set forth in SEQ ID NO:1 or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of PTP04 RNA in a sample by contacting the sample with a nucleic acid probe under conditions such that hybridization occurs and detecting the presence or amount of the probe bound to PTP04 RNA. The nucleic acid duplex formed between the probe and a nucleic acid sequence coding for a PTP04 polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container means having disposed therein a nucleic acid probe.

Another feature of the invention is a nucleic acid molecule as set forth in SEQ ID NO:1 or fragments thereof, comprising one or more regions that encode a PTP04 polypeptide or a PTP04 domain polypeptide, where the PTP04 polypeptide or the PTP04 domain polypeptide is fused to a non-PTP04 polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1 or a functional derivative thereof and a vector or a promoter effective to initiate transcription in a host cell. The recombinant nucleic acid can alternatively contain a transcriptional initiation region functional in a cell, a sequence complimentary to an RNA sequence encoding a PTP04 polypeptide and a transcriptional termination region functional in a cell.

Another aspect of the invention relates to a recombinant cell or tissue comprising a nucleic acid molecule encoding a PTP04 polypeptide. The recombinant cell may comprise a nucleic acid molecule encoding either a PTP04 polypeptide; a PTP04 domain polypeptide; or a PTP04 polypeptide or PTP04 domain polypeptide fused to a non-PTP04 polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified PTP04 polypeptide.

By "PTP04 polypeptide" it is meant an amino acid sequence substantially similar to the sequence shown in SEQ ID NO:2, or fragments thereof. A sequence that is substantially similar will preferably have at least 90% identity (more preferably at least 95% and most preferably 99–100%) to the sequence of SEQ ID NO:2.

The PTP04 polypeptides of the present invention preferably have a substantially similar biological activity to the protein encoded by the full length nucleic acid sequence set forth in SEQ ID NO:1 or to the proteins with amino acid sequence set forth in SEQ ID NO:2. By "biological activity" it is meant an activity of the PTP04 protein in a cell. The biological activity of the PTP04 is related to some of the activities of the cell which include, but are not limited to, cell proliferation motogenesis, metastasis, tumor escape, cell adhesion, transformation, or apoptosis.

The PTP04 polypeptides of the present invention preferably have a substantially similar biological activity to the protein encoded by the full length nucleic acid sequence set forth in SEQ ID NO:1 or to the proteins with amino acid sequence set forth in SEQ ID NO:2. By "biological activity" it is meant an activity of the PTP04 protein in a cell. The biological activity of the PTP04 is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid may, for example, comprise amino acid sequences encoded by a yeast or bacterial genome, or a cloning vector such as pUCl19. The term is meant to cover only those situations in which a person has intervened to elevate the proportion of the desired nucleic acid sequence.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect the invention features an isolated, enriched, or purified PTP04 polypeptide fragment.

By "a PTP04 polypeptide fragment" it is meant an amino acid sequence that is less than the full-length PTP04 amino acid sequence shown in SEQ ID NO:2. Examples of fragments include PTP04 domains, PTP04 mutants and PTP04-specific epitopes.

By "a PTP04 domain" it is meant a portion of the PTP04 polypeptide having homology to amino acid sequences from one or more known proteins wherein the sequence predicts some common function, interaction or activity. Well known examples of domains are the SH2 (Src Homology 2) domain (Sadowski, et al., *Mol. Cell. Biol.* 6:4396, 1986; Pawson and Schlessinger, *Curr. Biol.* 3:434, 1993), the SH3 domain (Mayer, et al., *Nature* 332:272, 1988; Pawson and Schlessinger, *Curr. Biol.* 3:434, 1993), and pleckstrin (PH) domain (Ponting, TIBS 21:245, 1996; Haslam, et al., *Nature* 363:309, 1993), all of which are domains that mediate protein:protein interaction, and the kinase catalytic domain (Hanks and Hunter, *FASEB J* 9:576–595, 1995). Computer programs designed to detect such homologies are well known in the art. The relative homology is at least 20%, more preferably at least 30% and most preferably at least 35%.

By a "PTP04 mutant" it is meant a PTP04 polypeptide which differs from the native sequence in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompassed by this term include, but are not limited to, (1) chimeric proteins which comprise a portion of a PTP04 polypeptide sequence fused to a non-PTP04 polypeptide sequence, for example a polypeptide sequence of hemagglutinin (HA), (2) PTP04 proteins lacking a specific domain, for example the catalytic domain, and (3) PTP04 proteins having a point mutation. A PTP04 mutant will retain some useful function such as, for example, binding to a natural binding partner, catalytic activity, or the ability to bind to a PTP04 specific antibody (as defined below).

By "PTP04-specific epitope" it is meant a sequence of amino acids that is both antigenic and unique to PTPO4. PTP04-specific epitope can be used to produce PTP04-specific antibodies, as more fully described below. Particularly preferred epitopes are shown in Example 4 below.

By "recombinant PTP04 polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:2; (b) the full length amino acid sequence of the sequence set forth in SEQ ID NO:2, except that it lacks one or more of the following segments of amino acid residues: 1–48, 49–294, 295–807 of SEQ ID NO:2; (c) the amino acid sequence set forth in SEQ ID NO:2 from amino acid residues, 1–48, 49–294, 295–807 of SEQ ID NO:2; or (d) the full length amino acid sequence set forth in SEQ ID NO:2 except that it lacks one or more of the domains selected from the group consisting of a signal peptide, an extracellular region, a transmembrane domain, a cytoplasmic domain, and a catalytic domain.

In yet another aspect the invention features an antibody (e.g., a monoclonal or polyclonal antibody) having specific binding affinity to a PTP04 polypeptide or PTP04 polypeptide fragment. By "specific binding affinity" is meant that the antibody binds to target (PTP04) polypeptides with greater affinity than it binds to other polypeptides under specified conditions. Antibodies having specific binding affinity to a PTP04 polypeptide may be used in methods for detecting the presence and/or amount of a PTP04 polypeptide in a sample by contacting the sample with the antibody under conditions such that an immunocomplex forms and detecting the presence and/or amount of the antibody conjugated to the PTP04 polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect the invention features a hybridoma which produces an antibody having specific binding affinity to a PTP04 polypeptide. By "hybridoma" is meant an immortalized cell line which is capable of secreting an antibody, for example a PTP04 antibody. In preferred embodiments the PTP04 antibody comprises a sequence of amino acids that is able to specifically bind a PTP04 polypeptide.

The invention features a method for identifying human cells containing a PTP04 polypeptide or a related sequence. The method involves identifying the novel polypeptide in human cells using techniques that are routine and standard in the art, such as those described herein for identifying PTP04 (e.g., cloning, Southern or Northern blot analysis, in situ hybridization, PCR amplification, etc.).

The invention also features methods of screening cells for natural binding partners of PTP04 polypeptides. By "natural binding partner" it is meant a protein that interacts with PTP04. Binding partners include ligands, agonists, antagonists and downstream signaling molecules such as adaptor proteins and may be identified by techniques well known in the art such as co-immunoprecipitation or by using, for example, a two-hybrid screen. (Fields and Song, U.S. Pat. No. 5,283,173, issued Feb. 1, 1994 and, incorporated be reference herein.) The present invention also features the purified, isolated or enriched versions of the polypeptides identified by the methods described above.

In another aspect, the invention provides a method for identifying a substance capable of modulating PTP04 activity comprising the steps of (a) contacting a PTP04 polypeptide with a test substance; and (b) determining whether the substance alters the activity of said polypeptide.

The invention also features another method of identifying substances capable of modulating the function of a PTP04 polypeptide. The method comprises the following steps: (a) expressing a PTP04 polypeptide in cells; (b) adding a compound to the cells; and (c) monitoring a change or an absence of a change in cell phenotype, cell proliferation, catalytic activity of the PTP04 polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity," in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate.

The term "substrate" as used herein refers to a molecule that is phoshorylated by or directly interacts with the protein kinase. The substrate is preferably a peptide and more preferably a protein. For example, in relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of a PTP04 polypeptide from a nucleic acid vector containing a PTP04 gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Change or the absence of change in cell phenotype is readily measured by techniques known in the art.

The term "cell proliferation" refers to the rate at which a group of cells divides. The number of cells growing in a vessel can be quantitated by a person skilled in the art when that person visually counts the number of cells in a defined area using a common light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding PTP04 polypeptides, nucleic acid vectors, recombinant cells, polypeptides, or antibodies of the invention.

In a preferred embodiment, the invention provides a method for treating or preventing an abnormal condition by administering a compound which is a modular of PTP04 function in vitro. The abnormal condition preferably involves abnormality in PTP04 signal transduction pathway, and most preferably is cancer. Such compounds preferably show positive results in one or more in vitro assays for an activity corresponding to treatment of the disease or disorder in question (such as the assays described in Example 6 below). Examples of substances that can be screened for favorable activity are provided in section XII below.

The summary of the invention described above is non-limiting and other features and advantages of the invention will be apparent from the following detailed description, and from the claims.

BRIEF DESCRIPTION OF THE FIGURES

FIG. 1 shows a comparison between the amino acid sequence of huma PTP04 and the amino acid sequence of the protein to which it is most closely related, murine ZPEP. The relative homology between the two (approximately 70%) suggests that the two proteins are members of the same PTP family but are not species orthologs.

DETAILED DESCRIPTION OF THE INVENTION

The present invention relates to the isolation and characterization of a new protein which we have called PTP04, nucleotide sequences encoding PTP04, various products and assay methods that can be used to identify compounds useful for the diagnosis and treatment of various PTP04 related diseases and conditions, for example cancer. Polypeptides derived from PTP04 and nucleic acids encoding such polypeptides may be produced using well known and standard synthesis techniques when given the sequences presented herein.

PTP04 is a tyrosine phosphatase with an apparent molecular weight of approximately 100 kDa. Primary sequence analysis shows that PTP04 is comprised of three domains: an N-terminal domain, a catalytic domain, and a C-terminal domain. The lack of a hydrophobic stretch of amino acids generally characterized as a transmembrane region indicates that PTP04 is a non-receptor tyrosine phosphatase.

The full-length PTP04 was originally isolated from a human leukemia cell line. Subsequent expression analysis of both normal tissues and cancer cell lines, shown in detail below, revealed that PTP04 is expressed in human thymus and has very low expression in other normal cells but is significantly overexpressed in a number of tumors, particularly in leukemias and lymphomas. This suggests that PTP04 plays an important role in the growth and persistence of these cancers.

The polypeptide and nucleotide sequences of the invention can be used, therefore, to identify modulators of cell growth and survival which are useful in developing therapeutics for various cell proliferative disorders and conditions, and in particular cancers related to inappropriate PTP04 activity. Assays to identify compounds that act intracellularly to enhance or inhibit PTP04 activity can be developed by creating genetically engineered cell lines that express PTP04 nucleotide sequences, as is more fully discussed below.

I. Nucleic Acids Encoding PTP04 Polypeptides

A first aspect of the invention features nucleic acid sequences encoding a PTP04 polypeptide. Included within the scope of this invention are the functional equivalents of the herein-described isolated nucleic acid molecules. Functional equivalents or derivatives can be obtained in several ways. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the PTP04 gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the PTP04 nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the PTP04 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Functional equivalents or derivatives of PTP04 can also be obtained using nucleic acid molecules encoding one or more functional domains of the PTP04 polypeptide. For example, the catalytic domain of PTP04 functions as an enzymatic remover of phosphate molecules bound onto tyrosine amino acids and a nucleic acid sequence encoding the catalytic domain alone or linked to other heterologous nucleic acid sequences can be considered a functional derivative of PTP04. Other functional domains of PTP04 include, but are not limited to, the proline-rich region within the N-terminal domain, and the C-terminal domain. Nucleic acid sequences encoding these domains are shown in SEQ. ID NO.:1 as follows: N-terminal domain 53–196; catalytic domain 197–934, C-terminal domain 935–2473.

II. A Nucleic Acid Probe for the Detection of PTP04

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modified in the sugar, phosphate or even the base portion as long as the probe still retains the ability to specifically hybridize under conditions as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such as polyacrylamide and latex beads, and nitrocellulose. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method And Kit For Detecting PTP04

One method of detecting the presence of PTP04 in a sample comprises (a) contacting the sample with the above-described nucleic acid probe, under conditions such that hybridization occurs, and (b) detecting the presence of the probe bound to the nucleic acid molecule. One skilled in the art would select the nucleic acid probe according to techniques known in the art as described above. Samples to be tested include but should not be limited to RNA samples of human tissue.

A kit for detecting the presence of PTP04 in a sample comprises at least one container having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymaticly labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art with or without a set of instructions concerning the use of such reagents in an assay.

IV. DNA Constructs Comprising a PTP04 Nucleic Acid Molecule and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and a nucleic acid molecule described herein. The present invention also relates to a nucleic acid molecule comprising a transcriptional region functional in a cell, a sequence complimentary to an RNA sequence encoding an amino acid sequence corresponding to a PTP04 polypeptide or functional derivative, and a transcriptional termination region functional in said cell. The above-described molecules may be isolated and/or purified DNA molecules.

The present invention also relates to a cell or organism that contains a PTP04 nucleic acid molecule as described herein and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a PTP04 gene may be obtained by the above-described cloning methods. This region may be retained for its transcriptional termination regulatory sequences, such as termination and polyadenylation. Thus, by retaining the 3'-region naturally contiguous to the DNA sequence encoding a PTP04 gene, the transcriptional termination signals may be provided. Where the transcriptional termination signals are not satisfactorily functional in the expression host cell, then a 3' region functional in the host cell may be substituted.

Two DNA sequences (such as a promoter region sequence and a PTP04 sequence) are said to be operably linked if the nature of the linkage between the two DNA sequences does not (1) result in the introduction of a frame-shift mutation, (2) interfere with the ability of the promoter region sequence to direct the transcription of a PTP04 gene sequence, or (3) interfere with the ability of the a PTP04 gene sequence to be transcribed by the promoter region sequence. Thus, a promoter region would be operably linked to a DNA sequence if the promoter were capable of effecting transcription of that DNA sequence. Thus, to express a PTP04 gene, transcriptional and translational signals recognized by an appropriate host are necessary.

The present invention encompasses the expression of a PTP04 gene (or a functional derivative thereof) in either prokaryotic or eukaryotic cells. Prokaryotic hosts are, generally, very efficient and convenient for the production of recombinant proteins and are, therefore, one type of preferred expression system for a PTP04 gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include lgt10, lgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli* and those from genera such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express PTP04 (or a functional derivative thereof) in a prokaryotic cell, it is necessary to operably link a PTP04 sequence to a functional prokaryotic promoter. Such promoters may be either constitutive or, more preferably, regulatable (i.e., inducible or derepressible). Examples of constitutive promoters include the int promoter of bacteriophage 1, the bla promoter of the b-lactamase gene sequence of pBR322, and the CAT promoter of the chloramphenicol acetyl transferase gene sequence of pPR325, and the like. Examples of inducible prokaryotic promoters include the major right and left promoters of bacteriophage 1 ($P_L$ and $P_R$), the trp, recA, lacZ, lacI, and gal promoters of *E. coli*, the a-amylase (Ulmanen et al., *J. Bacteriol.* 162:176–182, 1985) and the sigma-28-specific promoters of B. subtilis (Gilman et al., *Gene Sequence* 32:11–20(1984)), the promoters of the bacteriophages of Bacillus (Gryczan, In: The Molecular Biology of the Bacilli, Academic Press, Inc., N.Y. (1982)), and Streptomyces promoters (Ward et al., *Mol. Gen. Genet.* 203:468–478, 1986). Prokaryotic promoters are reviewed by Glick (*J. Ind. Microbiot.* 1:277–282, 1987); Cenatiempo (*Biochimie* 68:505–516, 1986); and Gottesman (*Ann. Rev. Genet.* 18:415–442, 1984).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404, 1981). The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the PTP04 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459, 1988). Alternatively, baculovirus vectors can be engineered to express large amounts of PTP04 in insects cells (Jasny, *Science* 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of PTP04.

A particularly preferred yeast expression system is that utilizing Schizosaccharmocyces pombe. This system is useful for studying the activity of members of the Src family (Superti-Furga, et al., *EMBO J.* 12:2625, 1993) and other NR-TKs.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of PTP04 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288, 1982); the TK promoter of Herpes virus (McKnight, *Cell* 31:355–365, 1982); the SV40 early promoter (Benoist et al., *Nature* (London) 290:304–310, 1981); the yeast gal4 gene sequence promoter (Johnston et al.,*Proc. Natl. Acad. Sci. (USA)* 79:6971–6975, 1982); Silver et al., *Proc. Natl. Acad. Sci. (USA)* 81:5951–5955, 1984).

Translation of eukaryotic mRNA is initiated at the codon which encodes the first methionine. For this reason, it is preferable to ensure that the linkage between a eukaryotic promoter and a DNA sequence which encodes PTP04 (or a functional derivative thereof) does not contain any intervening codons which are capable of encoding a methionine (i.e., AUG). The presence of such codons results either in a formation of a fusion protein (if the AUG codon is in the same reading frame as a PTP04 coding sequence) or a frame-shift mutation (if the AUG codon is not in the same reading frame as a PTP04 coding sequence).

A PTP04 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cell. Bio.* 3:280, 1983.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColEl, pSC101, pACYC 184, pVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pCl94, pC221, pT127, and the like. Such plasmids are disclosed by Gryczan (In: The Molecular Biology of the Bacilli, Academic Press, N.Y. (1982), pp. 307–329). Suitable Streptomyces plasmids include plJ101 (Kendall et al., *J. Bacteriol.* 169:4177–4183,1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704, 1986), and Izaki (Jpn. *J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204, 1982); Bollon et at., *J. Clin. Hematol. Oncol.* 10:39–48, 1980); Maniatis, In: *Cell Biology: A Comprehensive Treatise*, Vol. 3, *Gene Sequence Expression*, Academic Press, N.Y., pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of PTP04 or fragments or functional derivatives thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. PTP04 Polypeptides

Also a feature of the invention are PTP04 polypeptides. A variety of methodologies known in the art can be utilized to obtain the polypeptides of the present invention. They may be purified from tissues or cells which naturally produce them. Alternatively, the above-described isolated nucleic acid sequences can be used to express a PTP04 protein recombinantly.

Any eukaryotic organism can be used as a source for the polypeptide of the invention, as long as the source organism naturally contains such a polypeptide. As used herein, "source organism" refers to the original organism from which the amino acid sequence is derived, regardless of the organism the protein is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

A PTP04 protein, like all proteins, is comprised of distinct functional units or domains. In eukaryotes, proteins sorted through the so-called vesicular pathway (bulk flow) usually have a signal sequence (also called a leader peptide) in the N-terminus, which is cleaved off after the translocation through the ER (endoplasmic reticulum) membrane. Some N-terminal signal sequences are not cleaved off, remaining as transmembrane segments, but it does not mean these proteins are retained in the ER; they can be further sorted and included in vesicles. Non-receptor proteins generally function to transmit signals within the cell, either by providing sites for protein:protein interactions or by having some catalytic activity (contained within a catalytic domain), often both. Methods of predicting the existence of these various domains are well known in the art. Protein-:protein interaction domains can be identified by comparison to other proteins. The SH2 domain, for example is a protein domain of about 100 amino acids first identified as a conserved sequence region between the proteins Src and Fps (Sadowski, et al, *Mol. Cell. Bio.* 6:4396, 1986). Similar sequences were later found in many other intracellular signal-transducing proteins. SH2 domains function as regulatory modules of intracellular signaling cascades by interacting with high affinity to phosphotyrosine-containing proteins in a sequence specific and strictly phosphorylation-dependent manner (Mayer and Baltimore, *Trends Cell. Biol.* 3:8, 1993). Kinase or phosphatase catalytic domains can be identified by comparison to other known catalytic domains with kinase or phosphatase activity. See, for example Hanks and Hunter, *FASEB J.* 9:576–595, 1995.

Primary sequence analysis of the PTP04 amino acid sequence (shown in SEQ ID NO: 2) reveals that it does not contain a signal sequence or transmembrane domain and is, therefore, an intracellular protein. Comparison to known protein sequences revels that PTP04 is comprised of several unique domains. These include a 48 amino acid N-terminal domain (shown from amino acid number 1–48 of SEQ ID NO:2), a 245 amino acid catalytic domain (shown from amino acid number 49–294 of SEQ ID NO:2), and a 512 amino acid C-terminal domain (shown from amino acid number 295–807 of SEQ ID NO:2).

These PTP04 domains have a variety of uses. An example of such a use is to make a polypeptide consisting of the PTP04 catalytic domain and a heterologous protein such as glutathione S-transferase (GST). Such a polypeptide can be used in a biochemical assay for PTP04 catalytic activity useful for studying PTP04 substrate specificity or for identifying substances that can modulate PTP04 catalytic activity. Alternatively, one skilled in the art could create a PTP04 polypeptide lacking at least one of the three major domains. Such a polypeptide, when expressed in a cell, is able to form complexes with the natural binding partner(s) of PTP04 but unable to transmit any signal further downstream into the cell, i.e.,. it would be signaling incompetent and thus would be useful for studying the biological relevance of PTP04 activity. (See, for example, Gishizky, et al, *PNAS* :10889, 1995).

VI. An Antibody Having Binding Affinity To A PTP04 Polypeptide And A Hybridoma Containing the Antibody The present invention also relates to an antibody having specific binding affinity to a PTP04 polypeptide. The polypeptide may have the amino acid sequence set forth in SEQ ID NO:2, or a be fragment thereof, or at least 6 contiguous amino acids thereof. Such an antibody may be identified by comparing its binding affinity to a PTP04 polypeptide with its binding affinity to another polypeptide. Those which bind selectively to PTP04 would be chosen for use in methods requiring a distinction between PTP04 and other polypeptides. Such methods could include, but should not be limited to, the analysis of altered PTP04 expression in tissue containing other polypeptides and assay systems using whole cells.

A PTP04 peptide of the present invention can be used to produce antibodies or hybridomas. One skilled in the art will recognize that if an antibody is desired, such a peptide would be generated as described herein and used as an immunogen. Preferred PTP04 peptides for this purpose as shown in Example 4 below. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., *J. Immunol. Methods* 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or b-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp. Cell Res.* 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., *J. Histochem. Cytochem.* 18:315, 1970; Bayer, et al., *Meth. Enzym.* 62:308, 1979; Engval, et al., *Immunot.* 109:129, 1972; Goding, *J. Immunol. Meth.* 13:215, 1976). The labeled antibodies of the present invention can be used for in vitro, in vivo, and in in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., *Meth. Enzym.* 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, N.Y., pp. 289–307 (1992), and Kaspczak et al., Biochemistry 28:9230–8(1989).

VII. An Antibody Based Method And Kit For Detecting PTP04

The present invention encompasses a method of detecting a PTP04 polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels, either an increase or decrease, of PTP04 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: (i) a first container containing an above-described antibody, and (ii) second container containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Isolation of Natural Binding Partners of PTP04

The present invention also relates to methods of detecting natural binding partners capable of binding to a PTP04 polypeptide. A natural binding partner of PTP04 may be, for example, a substrate protein which is dephosphorylated as part of a signaling cascade. The binding parter(s) may be present within a complex mixture, for example, serum, body fluids, or cell extracts.

In general methods for identifying natural binding partners comprise incubating a substance with PTP04 and detecting the presence of a substance bound to PTP04. Preferred methods include the two-hybrid system of Fields and Song (supra) and co-immunoprecipitation.

IX. Identification of and Uses for Substances Capable of Modulating PTP04 Activity The present invention also relates to a method of detecting a substance capable of modulating PTP04 activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for PTP04 modulating activity are, for example but not limited to, thiazoles (see for example co-pending U.S. application Ser. Nos. 60/033,522, 08/660, 900), and naphthopyrones (U.S. Pat. No. 5,602,171).

In general the method comprises incubating cells that produce PTP04 in the presence of a test substance and detecting changes in the level of PTP04 activity or PTP04 binding partner activity. A change in activity may be manifested by increased or decreased phosphorylation of a PTP04 polypeptide, increased or decreased phosphorylation of a PTP04 substrate, or increased or decreased biological response in cells. A method for detecting modulation of PTP04 activity using the phosphorylation of an artificial substrate is shown in the examples below. Biological responses can include, for example, proliferation, differentiation, survival, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing PTP04 associated activity in a mammal comprising administering to said mammal an agonist or antagonist to PTP04 in an amount sufficient to effect said agonism or antagonism. Also encompassed in the present application is a method of treating diseases in a mammal with an agonist or antagonist of PTP04-related activity comprising administering the agonist or antagonist to a mammal in an amount sufficient to agonize or antagonize PTP04 associated function(s). The particular compound can be administered to a patient either by itself or in a pharmaceutical composition where it is mixed with suitable carriers or excipient(s). In treating a patient a therapeutically effective dose of the compound is administered. A therapeutically effective dose referes to that amount of the compound that results in amelioration of symptoms or a prolongation of survival in a patient.

Toxicity and therapeutic efficacy of such compounds can be determined by standard pharmaceutical procedures in cell cultures or experimental animals. For example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

X. Transgenic Animals

Also contemplated by the invention are transgenic animals useful for the study of PTP04 activity in complex in vivo systems. A variety of methods are available for the production of transgenic animals associated with this invention. DNA sequences encoding PTP04 can be injected into the pronucleus of a fertilized egg before fusion of the male and female pronuclei, or injected into the nucleus of an embryonic cell (e.g., the nucleus of a two-cell embryo) following the initiation of cell division (Brinster, et al., *Proc. Nat. Acad. Sci. USA* 82: 4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, *Experientia* 47: 897–905, 1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., *Cell* 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, "Teratocarcinomas and Embryonic Stem Cells, A Practical Approach", E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156, 1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel, et al., *Science* 244:1281–1288, 1989); and Simms, et al., *Bio/Technology* 6:179–183, 1988).

Thus, the invention provides transgenic, nonhuman mammals containing a transgene encoding a PTP04 polypeptide or a gene effecting the expression of a PTP04 polypeptide. Such transgenic nonhuman mammals are particularly useful as an in vivo test system for studying the effects of introducing a PTP04 polypeptide, regulating the expression of a PTP04 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human PTP04 polypeptide. Native expression in an animal may be reduced by providing an amount of anti-sense RNA or DNA effective to reduce expression of the receptor.

XI. Gene Therapy

PTP04 or its genetic sequences, both mutated and non-mutated, will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing a PTP04 coding sequence or a PTP04 mutant coding sequence as described above is inserted into cells, the cells are grown in vitro and then infused in large numbers into patients. In another preferred embodiment, a DNA segment containing a promoter of choice (for example a strong promoter) is transferred into cells containing an endogenous PTP04 in such a manner that the promoter segment enhances expression of the endogenous PTP04 gene (for example, the promoter segment is transferred to the cell such that it becomes directly linked to the endogenous PTP04 gene).

The gene therapy may involve the use of an adenovirus containing PTP04 cDNA targeted to an appropriate cell type, systemic PTP04 increase by implantation of engineered cells, injection with PTP04 virus, or injection of naked PTP04 DNA into appropriate cells or tissues, for example neurons.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant PTP04 protein into the targeted cell population (e.g., tumor cells or neurons). Methods which are well known to those skilled in the art can be used to construct recombinant viral vectors containing coding sequences. See, for example, the techniques described in Maniatis et al., "Molecular Cloning: A Laboratory Manual", Cold Spring Harbor Laboratory, N.Y. (1989), and in Ausubel et al., "Current Protocols in Molecular Biology", Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi MR, *Cell* 22:479–88, 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52, 1987); electroporation, wherein cells are exposed to large voltage pulses to introduce holes into the membrane (Chu G., et al., *Nucleic Acids Res.*, 15:1311–26, 1987); lipofection/ liposome fusion, wherein DNA is packaged into lipophilic vesicles which fuse with a target cell (Felgner PL., et al., *Proc. Natl. Acad. Sci. USA.* 84:7413–7, 1987)); and particle bombardment using DNA bound to small projectiles (Yang NS. et al., *Proc. Natl. Acad. Sci.* 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., Am. J. Respir. *Cell. Mol. Biol.*, 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a PTP04 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XII. Compounds that Modulate the Function of PTP04 Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridylquinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 Al), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. No. 08/702,232, filed Aug. 23, 1996, entitled "Indolinone Combinatorial Libraries and Related Products and Methods for the Treatment of Disease" by Tang et al. (Lyon & Lyon Docket No. 221/187) and Ser. No. 08/485,323, filed Jun. 7, 1995, entitled "Benzylidene-Z-Indoline Compounds for the Treatment of Disease" by Tang et al. (Lyon & Lyon Docket No. 223/298) and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. application Ser. No. 08/702,232, filed Aug. 23, 1996, entitled "Indolinone Combinatorial Libraries and Related Products and Methods for the Treatment of Disease" by Tang et al. (Lyon & Lyon Docket No. 221/187), Ser. No. 08/485,323, filed Jun. 7, 1995, entitled "Benzylidene-Z-Indoline Compounds for the Treatment of Disease" by Tang et al. (Lyon & Lyon Docket No. 223/298), and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating PTP04 activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 Al; Jones et al., U.S. Pat. No. 4,447,608; Kabbe et al., U.S. Pat. No. 4,757,072; Kaul and Vougioukas, U.S. Pat. No. 5, 316,553; Kreighbaum and Comer, U.S. Pat. No. 4,343,940; Pegg and Wardleworth, EPO Publication No. 0 562 734 Al; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., Br. *J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143: C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., *J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

EXAMPLES

Example 1

Isolation of cDNA Clones Encoding PTP04

The example below describes the isolation and identification of a new PTP sequence from primary cancer tissues and the subsequent cloning of a full-length human PTP04. Also described are probes useful for the detection of PTP04 in cells or tissues.

Materials and Methods:

Poly A+ RNA was isolated from 30 uM cryostat sections of frozen samples from primary human lung and colon carcinomas (Micro-FastTrack, InVitrogen, San Diego, Calif.). This RNA was used to generate single-stranded cDNA using the Superscript Preamplification System (GIBCO BRL, Gaithersburg, Md.; Gerard, GF et al. (1989), FOCUS 11, 66) under conditions recommended by the manufacturer. A typical reaction used 10 $\mu$g total RNA or 2 $\mu$g poly(A) RNA with 1.5 $\mu$g oligo(dT)$_{12-18}$ in a reaction volume of 60 $\mu$L. The product was treated with RNaseH and diluted to 100 $\mu$L with $H_2O$. For subsequent PCR amplification, 1–4 $\mu$L of this sscDNA was used in each reaction.

Degenerate oligonucleotides were synthesized on an Applied Biosystems 394 DNA synthesizer using established phosphoramidite chemistry, precipitated with ethanol and used unpurified for PCR. The sequence of the degenerate oligonucleotide primers follows:

PTPDFW=5'-GAYTTYTGGVRNATGRTNTGGGA- (sense) (SEQ ID NO:3) and

PTPHCSA=5'-CGGCCSAYNCCNGCNSWRCARTG -3' (antisense) (SEQ ID NO:4).

These primers were derived from the peptide sequences DFWXMXW(E/D) (SEQ ID NO:5) (sense strand from PTP catalytic domain) and HCXAGXG (antisense strand from PTP catalytic domain) (SEQ ID NO:6), respectively. Degenerate nucleotide residue designations are: N=A, C, G, or T; R=A or G; and Y=C or T.

PCR reactions were performed using degenerate primers applied to the single-stranded cDNA listed above. The primers were added at a final concentration of 5 $\mu$M each to a mixture containing 10 mM Tris HCl (pH8.3), 50 mM KCl, 1.5 MM $MgCl_2$, 200 $\mu$M each deoxynucleoside triphosphate, 0.001% gelatin, 1.5 U AmpliTaq DNA Polymerase (Perkin-Elmer/Cetus), and 1–4 $\mu$L cDNA. Following 3 min denaturation at 95° C., the cycling conditions were 94° C. for 30 s, 50° C. for 1 min, and 72° C. for 1 min 45 s for 35 cycles. PCR fragments migrating between 350–400 bp were isolated from 2% agarose gels using the GeneClean Kit (Bio101), and T-A cloned into the pCRII vector (Invitrogen Corp. U.S.A.) according to the manufacturer's protocol.

Colonies were selected for mini plasmid DNA-preparations using Qiagen columns and the plasmid DNA was sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., *J. Mol. Biol.* 215:403–10). One novel clone novel clone (G77-4a-117), designated PTP04, was isolated from human HLT370 primary lung carcinoma sample.

To obtain full-length cDNA encoding the novel phosphatase, RACE (rapid amplification of cDNA ends) was performed with sense or anti-sense oligonucleoides derived from the original PCR fragments. Marathon-Ready cDNA (Clontech, Palo Alto, Calif.) made from human Molt-4 leukemia cells was used in the RACE reactions with the following primers:

RACE primers:

5'-CACCGTTCGAGTATTTCAGATTGTGAAGAAG-TCC-3' (6595) (SEQ ID NO:7),

5'-GGACTTCTTCACAATCTGAAATACTCGAACGG TG-3' (6596) (SEQ ID NO:8),

5'-CCGTTATGTGAGGAAGAGCCACATTACAGGA CC-3' (6599) (SEQ ID NO:9),

5'-GGTCCTGTAATGTGGCTCTTCCTCACATAACG G-3' (6600) (SEQ ID NO:10),

AP-1, and AP-2 (Clontech).

RT-PCR Primers for PTP04:

5'-GGCATGCATGGAGTATGAAATGG-3' (6618) (SEQ ID NO:11),

5'-CGTACATCCCAGATGAGCTCAAGAATAGGG-3' (6632) (SEQ ID NO:12).

Isolated cDNA fragments encoding PTP04 were confirmed by DNA sequencing and subsequently used as probes for the screening of a human leukocyte cDNA library.

A human leukocyte cDNA library (lTriplEx, Clontech) and a Molt-4 leukemia cell library (lgt11, Clontech) were then screened to isolate full-length transcripts encoding PTP04. The 5' or 3'-RACE fragments were $^{32}$P-labeled by random priming and used as hybridization probes at $2\times10^6$ cpm/mL following standard techniques for library screening. Pre-hybridization (3 h) and hybridization (overnight) were conducted at 42° C. in 5×SSC, 5×Denhart's solution, 2.5% dextran sulfate, 50 mM $Na_2PO_4$/$NaHPO_4$ [pH 7.01], 50% formamide with 100 mg/mL denatured salmon sperm DNA. Stringent washes were performed at 65° C. in 0.1×SSC and 0.1% SDS. Several overlapping clones were isolated and found to span the sequence of the PCR fragment (G77-4a-117). The final sequence was verified by sequencing of both strains using a cycle sequencing dye-terminator kit with AmpliTaq DNA Polymerase, FS (ABI, Foster City, Calif.). Sequencing reaction products were run on an ABI Prism 377 DNA Sequencer.

Results:

The 3,580 bp human PTP04 nucleotide sequence encodes a polypeptide of 807 amino acids. The PTP04 coding sequence is flanked by a 52 nucleotide 5'-untranslated region and a 1086 nucleotide 3'-untranslated region ending with a poly(A) tail. While there are no upstream in frame stop codons, the first ATG beginning at nucleotide position 53 conforms to the Kozak consensus for an initiating methionine. This predicted first 6 amino acids are identical to those of murine ZPEP (SwissProt: P29352, GeneBank: M90388), further supporting this is the true translational start site. One cDNA clone had an insert after nucleotide 30 in the 5'UTR, but otherwise had no sequence differences.

The 807 amino acid sequence shows no signal sequence or a transmembrane domain and PTP04 is, therefore, an intracellular protein. PTP04 has an N-terminal region from amino acids 1–48, a catalytic domain from amino acids 49–294, and a C-terminal tail from amino acids 295–807. PTP04 is most related to murine ZPEP with an overall homology of 70%. ZPEP is a member of a subfamily of PTPs that includes PTP-PEST, HSC, BDP1 and PTP20, all of which are cytoplasmic PTPs with a single catalytic domain and a region rich in Pro, Glu, Ser and Thr residues (PEST domain). PTP04 also has a C-terminal PEST domain, from amino acids 495–807, where there are 57 serine residues (18%) and 35 proline residues(11%). A comparison of the amino acid sequences of PTP04 and ZPEP is shown in FIG. 1.

The homology between PTP04 and ZPEP is concentrated in the N terminal and C-terminal ends of the proteins with significant divergence in the middle. The N-terminal region of PTP04, from amino acids 1–48, is 81% homologous to murine ZPEP. The catalytic domain of PTP04, from amino acids 49–294, is 89% homologous to murine ZPEP. The region of PTP04 from 294–600 is approximately 50% homologous to murine ZPEP. The C-terminal region of PTP04, from 680–817, is 80% homologous to murine ZPEP. The human SuPTP04 sequence defines a novel member of the PTP-PEST subfamily of PTPs.

Example 2

Expression of PTP04

The example below shows the evaluation of PTP04 expression in normal human tissues and in cancer cell lines.

Materials and Methods:

Northern blots were prepared by running 20 $\mu$g total RNA per lane isolated from 22 human adult normal tissues (thymus, lung, duodenum, colon, testis, brain, cerebellum, salivary gland, heart, liver, pancreas, kidney, spleen, stomach, uterus, prostate, skeletal muscle, placenta, mammary gland, bladder, lymph node, adipose tissue), 2 human fetal normal tissues (fetal liver, fetal brain), and 24 human tumor cell lines (HOP-92, EKVX, NCI-H23, NCI-H226, NCI-H322M, NCI-H460, A549, HOP-62, OVCAR-3, OVCAR-4, OVCAR-5, OVCAR-8, IGROV1, SK-OV-3, SNB-19, SNB-75, U251, SF-268, SF-295, SF-539, CCRF-CEM, SR, DU-145, PC-3) (obtained from Nick Scuidero, National Cancer Institute, Developmental Therapeutics Program, Rockville, Md). The total RNA samples were run on a denaturing formaldehyde 1% agarose gel and transferred onto a nitrocellulose membrane (BioRad, Calif.). An additional human normal tissue Northern blot containing 2 $\mu$g polyA+ MRNA per lane from 8 different human cancer cell lines (NCI-H522, K-562, MOLT-4, HL-60, S3, Raji, SW480, G361) on a charge-modified nylon membrane (human cancer cell line blot #7757–1, Clontech, Palo Alto, Calif.) were also hybridized.

For the total RNA samples, nitrocellulose membranes were hybridized with randomly primed [a-$^{32}$P]dCTP-labeled probes synthesized from a 579 bp StuI-BstXI fragment of pCR2.1.mini298. Hybridization was performed overnight at 42° C. in 4×SSPE, 2.5×Denhardt's solution, 50% formamide, 0.2 mg/mL denatured salmon sperm DNA, 0.1 mg/mL yeast tRNA (Boehringer Mannheim,Ind.), 0.2% SDS, with 5×10$^6$ cpm/mL of [a-$^{32}$P]dCTP labeled DNA probes on a Techne hybridizer HB-1. The blots were washed with 2×SSC, 0.1% SDS, at 65° C. for 20 min twice followed by in 0.5×SSC, 0.1% SDS at 65° C. for 20 min. The blots were exposed to a phospho-imaging screen for 24 hours and scanned on a Molecular Dynamics Phosphoimager SF.

A 351 bp EcoRI-HindIII fragment of G77–4a-117 was used to generate a probe for 2 $\mu$g poly A+mRNA samples on a Clontech nylon membrane. Hybridization was performed at 42° C. overnight in 5×SSC, 2% SDS, 10×Denhardt's solution, 50% formamide, 100 $\mu$g/mL denatured salmon sperm DNA with 1–2×10$^6$ cpm/mL of [a-$^{32}$P]dCTP -labeled DNA probes. The membrane was washed at room temperature in 2×SSC/0.05% SDS for 30 min and followed by at 50° C. in 0.2×SSC/0.1% SDS for 30 min, twice, and exposed for 48 hours on Kodak XAR-2 film.

RT-PCR Detection of Novel PTPS

Total RNA was isolated from various cell lines or fresh frozen tissues by centrifugation thrugh a cesium chloride cushion. Twenty $\mu$g of total RNA was reverse transcribed with random hexamers and Moloney murine leukemia virus reverse transcriptase (Super-ScriptII, GIBCO BRL, Gaithersburg, Md.). PCR was then used to amplify cDNA encoding SuPTP04. RT-PCR reactions lacking only the reverse transcriptase were performed as controls. PCR products were electrophoresed on 3% agarose gels, visualized by ethidium bromide staining and photographed on a UV light box. The intensity for a 270-bp fragment specific to PTP04 were compared among different RNA samples.

Results:

A single SuPTP04 mRNA transcript of approximately 4.5 kb was identified by Northern analysis, and found to be exclusively in the Thymus. The rest of 23 human normal tissues (fetal brain, fetal liver, lung, duodenum, colon, testis, brain, cerebellum, salivary gland, heart, liver, pancreas, kidney, spleen, stomach, uterus, prostate, skeletal muscle, placenta, mammary gland, bladder, lymph node, adipose tissue) were all negative. Six of the human tumor cell lines (CCRF-CEM, K-562, MOLT-4, HL-60, SR, Raji) were positive. The rest of 26 human tumor cell lines were negative. RT-PCR with gene specific primer-pairs showed that expression of the transcripts encoding SuPTP04 confirmed the results from Northern analysis and also detected low levels in adipose, kidney, small intestine, hematopoietic tissues and various cell types (spleen, thymus, lymph node, bone marrow, peripheral leukocytes and lymphocytes.

The selective expression of PTP04 in cells of hematopoetic origin including normal human thymus and several leukemia cell lines suggests a potential involvement in immune regulation including T and B cell survival, differentiation or co-stimulation, and/or inflammatory, immunosuppressive or autoimmune disorders. Additionally, expression in adipose tissue suggests a possible role in metabolic disorders such as diabetes.

Example 3

Recombinant Expression of PTP04

The following example illustrates the construction of vectors for expression of recombinant PTP04 and the creation of recombinant cell lines expressing PTP04.

Construction of Expression Vectors

Expression constructs were generated by PCR-assisted mutagenesis in which the entire coding domains of PTP04 was tagged on its carboxy-terminal end with the hemophilus influenza hemaglutinin (HA) epitope YPYDVPDYAS (SEQ ID NO:13) (Pati, 1992). The construct was introduced into two mammalian expression vectors: pLXSN (Miller, A. D. & Rosman, G. J., *Biotechniques* 7, 980–988, 1989) for the generation of virus producing lines; and pRK5 for transient expression in mammalian.

Dominant negative (signaling incompetent) PTP04 constructs were also made in both pLXSN and pRK5 by mutation of the invariant Cys in the conserved HCSAG (SEQ ID NO:14) motif to an Ala by PCR mutagenesis.

The entire PTP04 open reading frames (no HA-tag) excluding the initiating methionines were generated by PCR and ligated into PGEX vector (Pharmacia Biotech, Uppsala, Sweden) for bacterial production of GST-fusion proteins for immunization of rabbits for antibody production. The entire PTP04 open reading frame excluding the initiating methionines was generated by PCR and ligated into PGEX vector for bacterial production of GST-fusion proteins for immunization of rabbits for antibody production. This vector contains the glutathione-S-transferase coding sequence followed by a polylinker for generating recombinant fusion proteins. The GST moiety comprises the N-terminal portion of the fusion protein.

Transient Expression in Mammalian Cells

The pRK5 expression plasmids (10 $\mu$g DNA/100 mm plate) containing the HA-tagged PTP04 gene can be introduced into COS and 293 cells with lipofectamine (Gibco BRL). After 72 hours, the cells were harvested in 0.5 mL solubilization buffer (20 mM HEPES pH7.35, 150 mM NaCl, 10% glycerol, 1% Triton X-100, 1.5 mM MgCl$_2$, 1 mM EGTA, 2 mM phenylmethylsulfonyl fluoride, 1 $\mu$g/mL aprotinin). Sample aliquots were resolved by SDS polyacrylamide gel electrophoresis (PAGE) on 15% acrylamide/0.5% bis-acrylamide gels and electrophoretically transferred to nitrocellulose. Non-specific binding was blocked by pre-incubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various PTP04-specific antisera.

Generation of Virus Producing Cell Lines pLXSN recombinant constructs containing the PTP04 gene were transfected into an amphotropic helper cell line PA317 using CaCl$_2$ mediated transfection. After selection on G418, the cells were plated on normal media without G418 (500 μg/mL). Supernatants from resistant cells were used to infect the ecotropic helper cell line GP+E86, and cells again selected on G418. Resistant cells were again taken off G418, and the supernatants harvested every 8–12 hours and pooled as virus stock. Redemann et al., 1992, *Mol. Cell. Biol.* 12: 491–498. Viral stock titers were typically ~10$^6$/mL.

Stable Expression in Mammalian Cells

NIH-3T3, and BALB/3T3 cells were grown in 100 mm plates with DMEM (Gibco) containing 10% fetal calf serum (FCS). The cells were superinfected with the PTP04 retrovirus by adding approximately 3 mL viral supernatant to 15 mL culture media for approximately 24 hours. Cells expressing the retroviral constructs were then selected by growth in DMEM/10% FCS supplemented with 500 μg/mL G418.

Example 4

Generation of Anti-PTP04 Antibodies

PTP04-specific immunoreagents were raised in rabbits against a mixture of three KLH-conjugated synthetic peptides corresponding to unique sequences present in human PTP04. The peptides (see below) were conjugated at the C-terminal residue with KLH.

peptide 428A: SWPPSGTSSKMSLDDLPEKQDGTVF-PSSLLP (SEQ ID NO:15)

peptide 429A: YSLPYDSKHQIRNASNVKHHDSSAL-GVYSY (SEQ ID NO:16)

peptide 430A: HTLQADSYSPNLPKSTTKAAKMMN-QQRTKC (SEQ ID NO:17)

Additional immunoreagents were generated by immunizing rabbits with the bacterially expressed entire coding region of PTP04 expressed as a GST-fusion protein. GST fusion proteins were produced in DH5-alpha *E. coli* bacteria as described in Smith, et al. *Gene* 67:31, 1988. Bacterial protein lysates were purified on glutathione-sepharose matrix as described in Smith, et al., supra.

Example 5

Assay for PTP04 Activity

Materials and Methods:

Recombinant wild-type and dominant negative (signaling incompetent) PTP04 (see Example 3, supra) were purified from bacteria as GST-fusion proteins. Lysates were bound to a glutathione-sepharaose matrix and washed twice with 1xHNTG, followed by one wash with a buffer containing 100 mM 2-(N-morpholino)ethansulfonic acid (MES), pH 6.8, 150 mM NaCl, and 1 mM EDTA.

The assay for phosphatase activity was essentially done as described by Pei et al.(1993) using p-nitrophenolphosphate (PNPP) as a generic PTP substrate. Briefly, after the last washing step, reactions were started by adding 50 mL Assay Buffer (100 mM MES pH 6.8, 150 mM NaCl, 10 mM DTT, 2 mM EDTA, and 50 mM PNPP) to the matrix bound proteins. Samples were incubated for 20 min. at 23° C. The reactions were terminated by mixing 40 μL of each sample with 960 μL 1 N NaOH, and the absorbance of p-nitrophenol was determined at 450 nm. To control for the presence of PTP04 in the precipitates, the precipitates were boiled in SDS sample buffer and analyzed by SDS-PAGE. The presence of PTP04 was then detected by immunoblot analysis with anti-PTP04 antibodies.

Example 6

Screening Systems for the Identification of Inhibitors of PTP04 Activity

Assays may be performed in vitro or in vivo and are described in detail herein or can be obtained by modifying existing assays, such as the growth assay described in patent application Ser. No. 08/487,088 (Lyon & Lyon Docket No. 212/276), filed Jun. 7, 1995, by Tang et al., and entitled "Novel Pharmaceutical Compounds," or the assays described in patent application Ser. No. 60/005,167 (Lyon & Lyon Docket No. 215/256), filed Oct. 13, 1995 by Seedorf et al., and entitled "Diagnosis and Treatment of TKA-1 related disorders," all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acide alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified to form a second nucleic acid sequence, encoding the same polypeptide as endoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans. Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated, enriched or purified nucleic acid molecule comprising a nucleotide sequence that
   (a) encodes a polypeptide comprising the full length amino acid sequence set forth in SEQ ID NO:2; or
   (b) is a nucleotide sequence that is completely complementary to the nucleotide sequence of (a).

2. The nucleic acid molecule of claim 1, wherein said nucleic acid molecule is isolated, enriched, or purified from a mammal.

3. The nucleic acid molecule of claim 2, wherein said mammal is a human.

4. The nucleic acid molecule of claim 1, further comprising a vector or promoter effective to initiate transcription in a host cell.

5. The nucleic acid molecule of claim 1, further comprising a nucleic acid region that encodes a second polypeptide, wherein said region is fused to said nucleic acid molecule.

6. A recombinant cell comprising the nucleic acid molecule of claim 5.

7. An isolated, enriched or purified nucleic acid molecule comprising the nucleotide sequence set forth in SEQ ID NO:1.

8. The nucleic acid molecule according to claim 1, wherein said nucleic acid molecule further comprises restriction endonuclease recognition sites at the 5' end and/or 3' end of the nucleic acid molecule.

9. The nucleic acid molecule according to claim 4, wherein said vector is pLXSN or pRK5.

10. The nucleic acid molecule according to claim 4, wherein said vector is pGEX.

11. The nucleic acid molecule according to claim 5, wherein said nucleic acid molecule further comprises a foreign nucleic acid sequence which encodes a secretion and/or processing sequence,
    so that the nucleic acid molecule encodes a heterologous protein which may be further processed and/or secreted from a cell.

12. The recombinant cell according to claim 6, wherein said nucleic acid molecule further comprises a foreign nucleic acid sequence which encodes a secretion and/or processing sequence,
    so that the nucleic acid molecule encodes a heterologous protein which may be further processed and/or secreted from the recombinant cell.

13. The recombinant cell according to claim 6, wherein said recombinant cell is prokaryotic.

14. The recombinant cell according to claim 6, wherein said recombinant cell is eukaryotic.

15. The recombinant cell according to claim 6, wherein said recombinant cell is at least one of a COS cell line, a 293 cell line, a PA 317 cell line, an NIH-3T3 cell line or a BALB/3T3 cell line.

* * * * *